(12) United States Patent
Hayashi et al.

(10) Patent No.: US 9,814,628 B2
(45) Date of Patent: Nov. 14, 2017

(54) SEPARATING DEVICE AND SEPARATING METHOD OF MATERIAL OF ABSORBENT ARTICLE

(71) Applicant: UNICHARM CORPORATION, Ehime (JP)

(72) Inventors: Tomoki Hayashi, Kagawa (JP); Hidetaka Oyama, Kagawa (JP); Masashi Kagawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 69 days.

(21) Appl. No.: 14/440,076

(22) PCT Filed: Oct. 24, 2013

(86) PCT No.: PCT/JP2013/078795
§ 371 (c)(1),
(2) Date: May 1, 2015

(87) PCT Pub. No.: WO2014/069319
PCT Pub. Date: May 8, 2014

(65) Prior Publication Data
US 2015/0314486 A1 Nov. 5, 2015

(30) Foreign Application Priority Data

Nov. 2, 2012 (JP) ................................. 2012-243051

(51) Int. Cl.
*B07B 9/00* (2006.01)
*B29B 17/02* (2006.01)
(Continued)

(52) U.S. Cl.
CPC ........ *A61F 13/15617* (2013.01); *B02C 23/30* (2013.01); *B07B 1/20* (2013.01);
(Continued)

(58) Field of Classification Search
CPC ................ B29B 17/02; B29B 17/0412; B29B 2017/0203; B07B 15/00; B07B 9/00;
(Continued)

(56) References Cited

U.S. PATENT DOCUMENTS 3,079,095 A * 2/1963 Beards ...................... B02C 4/08
241/230
3,784,007 A * 1/1974 Skrmetta ................. B07B 13/07
209/674
(Continued)

FOREIGN PATENT DOCUMENTS

CN 1137245 A 12/1996
CN 1149262 A 5/1997
(Continued)

OTHER PUBLICATIONS

Office Action in CN Application No. 201380056994.2, dated May 3, 2016.
(Continued)

*Primary Examiner* — James S McClellan
*Assistant Examiner* — Peter Iannuzzi
(74) *Attorney, Agent, or Firm* — Hauptman Ham, LLP

(57) ABSTRACT

A separating device separates liquid absorbent fibers from a material including the liquid absorbent fibers of an absorbent article and impurities. The separating device includes: a case; an insertion port for inserting the material into the case on an airflow; a rotation member in the case for agitating and opening the material; and a discharge port for discharging the liquid absorbent fibers from inside the case on an airflow. The rotation member has a revolving axis with an axial direction along a predetermined direction from the insertion port to the discharge port, and a shaft member rotating around a rotating axis that has been set with an axial direction along the predetermined direction, while revolving (Continued)

around the revolving axis. The shaft member has protruding sections protruding outward and intersecting with an axial direction of the shaft member.

10 Claims, 14 Drawing Sheets

(51) Int. Cl.
| | | |
|---|---|---|
| *A61F 13/15* | (2006.01) | |
| *B07B 15/00* | (2006.01) | |
| *B02C 23/30* | (2006.01) | |
| *B07B 4/02* | (2006.01) | |
| *B07B 1/20* | (2006.01) | |
| *B07B 13/07* | (2006.01) | |
| *B29L 31/48* | (2006.01) | |
| *B07B 1/00* | (2006.01) | |
| *B07B 4/08* | (2006.01) | |

(52) U.S. Cl.
CPC ............ *B07B 4/02* (2013.01); *B07B 9/00* (2013.01); *B07B 13/07* (2013.01); *B07B 15/00* (2013.01); *B29B 17/02* (2013.01); *B07B 1/00* (2013.01); *B07B 4/08* (2013.01); *B29B 2017/0203* (2013.01); *B29B 2017/0234* (2013.01); *B29L 2031/4878* (2013.01); *Y02W 30/622* (2015.05)

(58) Field of Classification Search
CPC .... B07B 4/08; B07B 4/02; B07B 1/00; B02C 23/08; A61F 13/15617; B09B 5/00; B29K 2105/26; Y02W 30/622; B29L 2031/4878; D21B 1/026; D21B 1/028
USPC ......... 241/236, 159, 60, 62, 18, 19, 81, 175, 241/188.1; 209/22, 24, 300, 305, 306
See application file for complete search history.

(56) References Cited

U.S. PATENT DOCUMENTS

| | | | | |
|---|---|---|---|---|
| 4,500,040 A | * | 2/1985 | Steffens | B29B 17/02 241/14 |
| 5,593,096 A | * | 1/1997 | Harker | B02C 13/04 241/14 |
| 2003/0189116 A1 | * | 10/2003 | McCamley | B03B 9/065 241/24.19 |

FOREIGN PATENT DOCUMENTS

| | | | |
|---|---|---|---|
| EP | 0091982 A2 | 10/1983 | |
| EP | 0739657 A1 | 10/1996 | |
| JP | EP 0739657 A1 * | 10/1996 | ............ B03B 9/061 |
| JP | 11-235575 A | 8/1999 | |
| JP | 2001-336077 A | 12/2001 | |
| JP | 2003-200147 A | 7/2003 | |
| JP | 2004-313878 A | 11/2004 | |
| JP | 2006-272203 A | 10/2006 | |
| JP | 2006-274201 A | 10/2006 | |
| JP | 2009-262088 A | 11/2009 | |

OTHER PUBLICATIONS

Extended European Search Report in EP Application No. 13850623.3, dated Jun. 27, 2016.
International Search Report and Written Opinion dated Jan. 28, 2014 in International Application No. PCT/JP2013/078795.
International preliminary report on patentability and Written Opinion dated May 14, 2015, corresponding to PCT/JP2013/078795.

\* cited by examiner

C-C ARROW VIEW

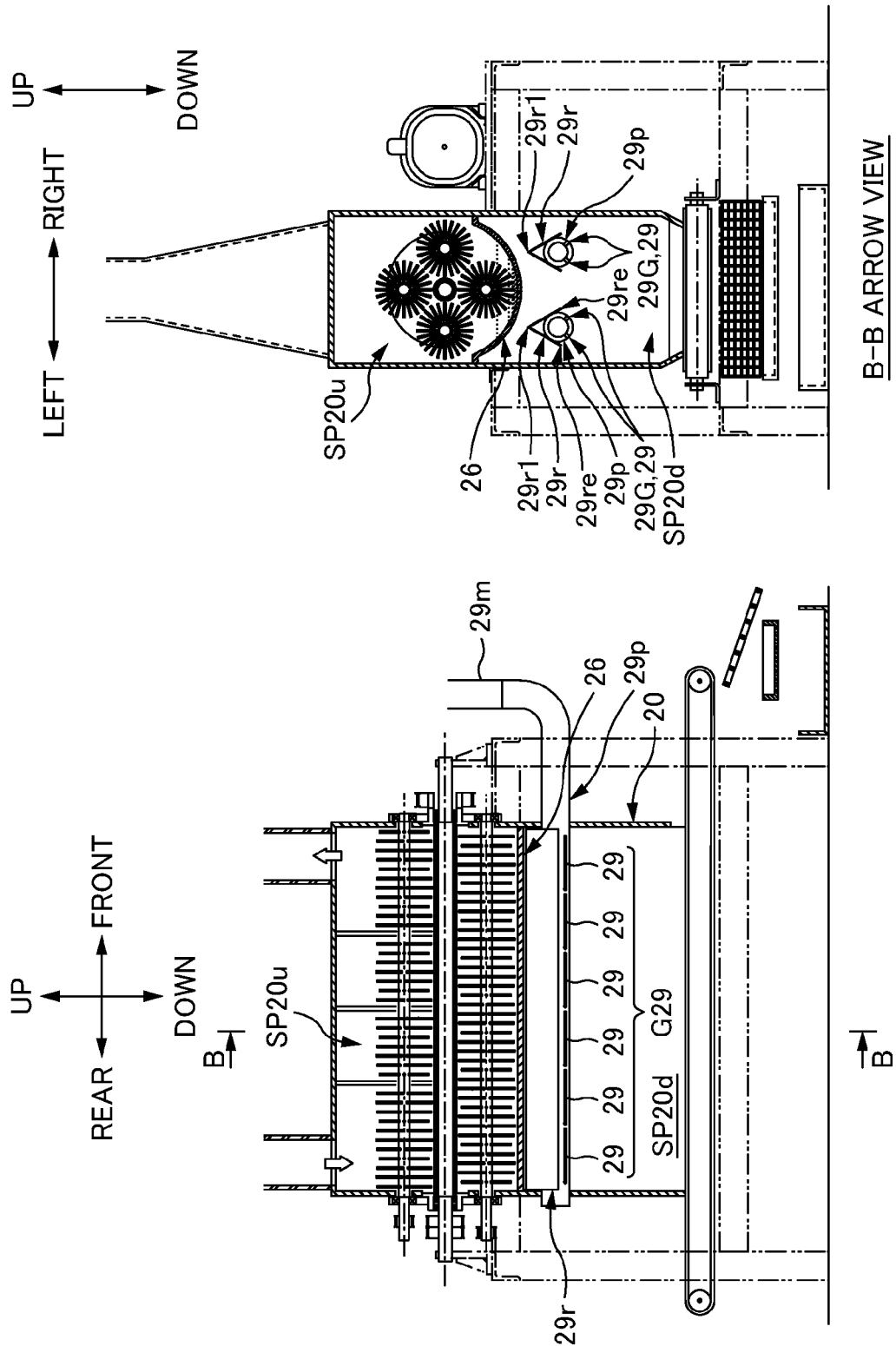

SEPARATING DEVICE AND SEPARATING METHOD OF MATERIAL OF ABSORBENT ARTICLE

RELATED APPLICATIONS

The present application is a National Phase of International Application Number PCT/JP2013/078795, filed Oct. 24, 2013, and claims priority of Japanese Patent Application No. 2012-243051 filed on Nov. 2, 2012.

TECHNICAL FIELD

The present invention relates to separating devices that separate liquid absorbent fibers such as pulp fibers from a material of an absorbent article such as a disposable diaper, and separating methods thereof.

BACKGROUND ART

Conventionally, as a material of an absorbent article such as a disposable diaper and a sanitary napkin, liquid absorbent fibers such as pulp fibers and superabsorbent polymers (hereinbelow, referred to as SAP) and the like have been used.

Recently, from the viewpoint of recycling of resources, waste material such as defective articles of absorbent articles and defective articles of absorbent bodies are not disposed of as is, but the pulp fibers, the SAP and the like that can be recycled are collected from the waste material.

Regarding this point, PTL 1 discloses a device that separates and collects the pulp fibers and the SAP from the waste material in which the pulp fibers, the SAP and the like are mixed.

In more detail, this device has a case, and inside the case are housed three rotation members for opening fiber. Further, a ceiling section of the case is provided with an insertion port and a discharge port, and a lattice member is provided as a bottom section. The waste material is inserted from the insertion port into the case while riding on an airflow, and this waste material is opened with the above three rotation members. The pulp fibers of the waste material that have been opened ride on the airflow and are discharged from the discharge port and collected, and on the other hand the SAP and the like with a higher specific gravity than the pulp fibers are passed through openings of the lattice member that is the bottom section and dropped and collected.

Here, with this device, the rotation axis of each of the three rotation members is facing a direction (hereinafter, referred to also a left-right direction) that is orthogonal to a predetermined direction (hereinafter, also referred to as a front-rear direction) from the insertion port to the discharge port. Further, a peripheral surface of the rotation member has a rectangular plate row formed with a plurality of rectangular plates arranged in a row in a comb-form in a predetermined pitch in a direction along the rotation axis, and a plurality of rows of the comb-form rectangular plate rows are provided in a predetermined pitch in a circumferential direction of the rotation member.

CITATION LIST

Patent Literature

PTL1 Japanese Patent Application Laid-open Publication No. 2001-336077

SUMMARY

Technical Problem

On the other hand, a device in a reference example shown in FIG. 1A and FIG. 1B can also be conceived. FIG. 1A is a schematic vertical cross sectional view, and FIG. 1B is a B-B arrow view in FIG. 1A. Here, with the device in this reference example, a rotation axis C130 of a rotation member 130 is set along a front-rear direction, in other words a direction from the insertion port 122 toward the discharge port 124, and below that is arranged the above-described lattice member 140.

According to the device in this reference example, as in FIG. 1A, since the plurality of rectangular plates 133 are arranged in a comb-form in one line along the front-rear direction, the waste material inserted from the insertion port 122 is hit a number of times with the above rectangular plates 133, 133 . . . lined up in many levels, while being sent to the discharge port 124 along the front-rear direction. Thus, the device in the reference example in FIG. 1A, in comparison to the device in PTL 1, is considered to be able to exert a relatively high opening performance, regardless of the fact that the number of the rotation member 130 is one which is a small number.

However, in the manufacturing factory, product efficiency and pursuit of product efficiency is being pursued daily, and the device in the reference example has also been further required to improve its opening performance.

The present invention was made in view of the above described problems and an object is to increase opening performance of a separating device and to increase its separating performance.

Solution to Problem

An aspect of the invention is a separating device that separates liquid absorbent fibers from a material including the liquid absorbent fibers of an absorbent article and impurities, the separating device including:

a case;

an insertion port for inserting the material into the case, while the material is made to ride on an airflow;

a rotation member housed in the case, the rotation member agitating and opening the material; and a discharge port for discharging the liquid absorbent fibers, of the material that has been opened with the rotation member, from inside the case, while the liquid absorbent fibers are made to ride on an airflow, and the rotation member having a revolving axis and a shaft member, the revolving axis being set with an axial direction along a predetermined direction from the insertion port to the discharge port, the shaft member rotating around a rotating axis that has been set with an axial direction along the predetermined direction, while revolving around the revolving axis, the shaft member having protruding sections that protrude outward in a direction that intersects with an axial direction of the shaft member.

Further, a separating method of separating liquid absorbent fibers from a material having the liquid absorbent fibers of an absorbent article and impurities, the method including:

inserting the material into the case from an insertion port, while the material is made to ride on an airflow;

agitating and opening the material with a rotation member housed inside the case; and discharging the liquid absorbent fibers, of the material that has been opened with the rotation member, from inside the case via a discharge port, while the liquid absorbent fibers are made to ride on an airflow, in the agitating and the opening of the material, using a shaft member as the rotation member, the shaft member being set with an axial direction along a predetermined direction from the insertion port to the discharge port, the shaft member having protruding sections that protrude outward in a direction that intersects with the axial direction, the shaft member rotating around a rotating axis that has been set with an axial direction along the predetermined direction, while revolving around the revolving axis that has been set along the predetermined direction.

Other features of the present invention will be made clear through the present specification with reference to the accompanying drawings.

Advantageous Effects of Invention

According to this invention, an opening performance of a separating device can be increased, and a separating property thereof can be improved.

BRIEF DESCRIPTION OF DRAWINGS

FIG. 8A is a schematic vertical sectional view showing a modified example of a suction port 29, and FIG. 8B is a B-B arrow view in FIG. 8A.

DESCRIPTION OF EMBODIMENTS

Figure 1B:
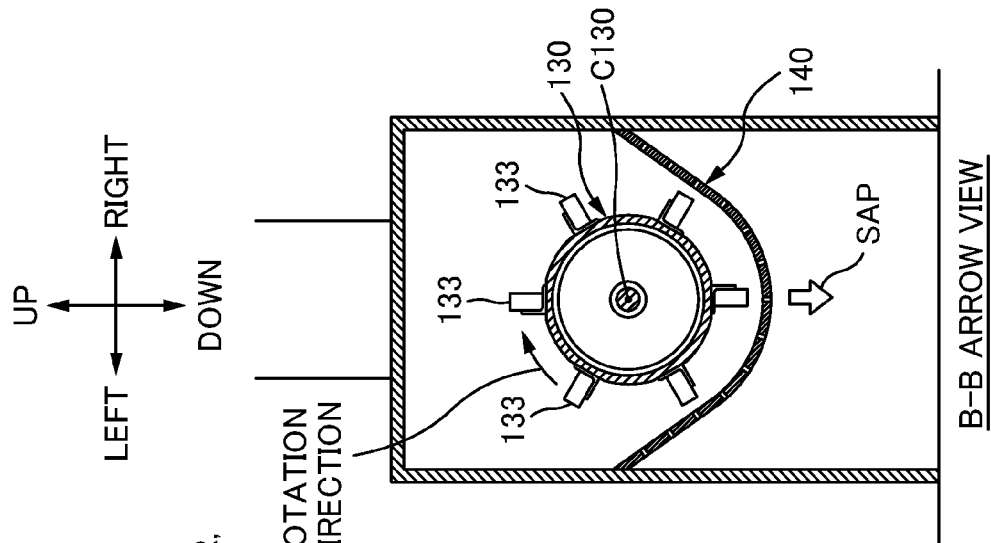
FIG. 1B is a B-B arrow view in FIG. 1A.
Figure 1A:
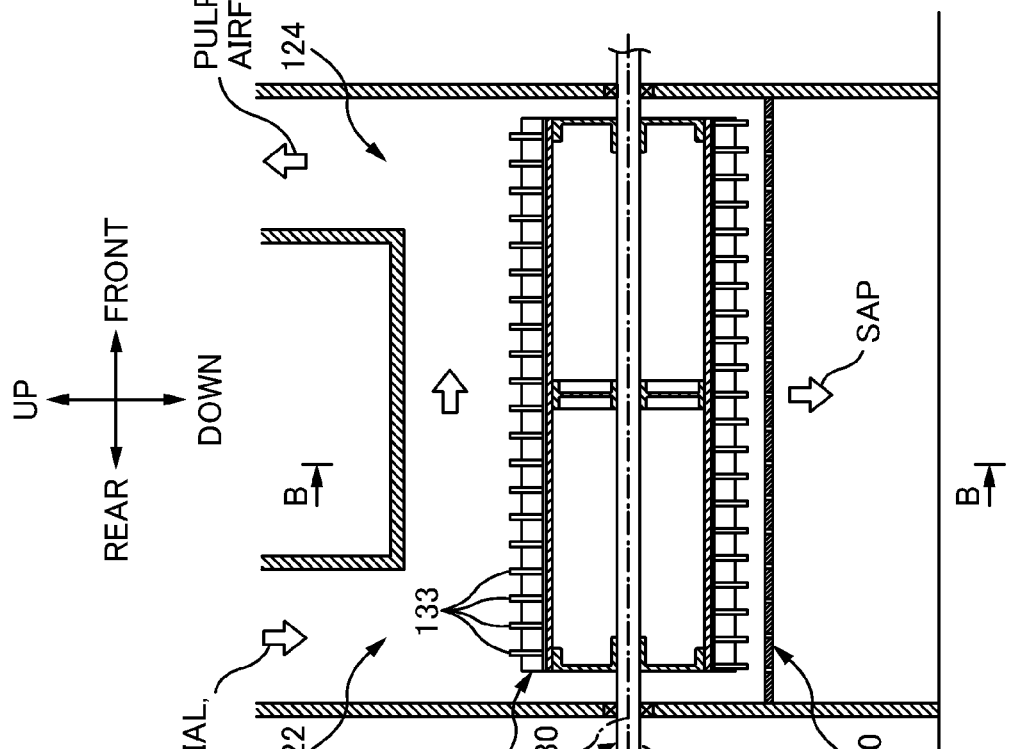
FIG. 1A is a schematic vertical sectional view of a separating device in a reference example.

At least the following matters will become clear with reference to this specification and the attached drawings.

A separating device that separates liquid absorbent fibers from a material including the liquid absorbent fibers of an absorbent article and impurities, the separating device comprising:

a case;

an insertion port for inserting the material into the case, while the material is made to ride on an airflow;

a rotation member housed in the case, the rotation member agitating and opening the material; and a discharge port for discharging the liquid absorbent fibers, of the material that has been opened with the rotation member, from inside the case, while the liquid absorbent fibers are made to ride on an airflow, and the rotation member having a revolving axis and a shaft member, the revolving axis being set with an axial direction along a predetermined direction from the insertion port to the discharge port, the shaft member rotating around a rotating axis that has been set with an axial direction along the predetermined direction, while revolving around the revolving axis, the shaft member having protruding sections that protrude outward in a direction that intersects with an axial direction of the shaft member.

With such a separating device of a material of an absorbent article, the rotation member has the shaft member having the protruding section. Then, this shaft member rotates and revolves, and thus hits the material with the protruding sections, and mixes and opens the material. Thus, a high opening performance can be obtained, and as a result the separating property of liquid absorbent fibers from the material can be improved.

A separating device of a material of an absorbent article, wherein preferably the rotation member has a plurality of the shaft members arranged in a revolving direction, each of the shaft members has a protruding section group formed with a plurality of the protruding sections arranged radially in a rotating direction in a plurality of positions in an axial direction of the shaft members.

With such a separating device of a material of an absorbent article, the plurality of the above shaft members are included that rotate and revolve, and further each of the shaft members has the above protruding section group in the plurality of positions in the axial direction. Thus, the hitting frequency of the material can be increased, and as a result the opening performance can be further improved.

A separating device of a material of an absorbent article, wherein preferably in respect to the protruding section groups adjacent to each other in an axial direction of the shaft member, arrangement positions of the protruding sections with respect to each other are shifted in the rotating direction.

With such a separating device of a material of an absorbent article, immediately after the protruding sections belonging to a predetermined protruding section group have hit the material, the protruding sections belonging to the protruding section groups positioned adjacent in the axial direction can again hit this material. Thus, the hitting frequency of the material can be further increased.

A separating device of a material of an absorbent article, wherein preferably in respect to the shaft members adjacent to each other in the revolving direction, arrangement positions of the protruding section groups with respect to each other are shifted in the axial direction.

With such a separating device of a material of an absorbent article, immediately after the protruding sections of the protruding section group of the predetermined shaft member have hit the material, with the protruding sections of the protruding section group of the shaft member positioned adjacent in the revolving direction the material can be hit again. Thus, the hitting frequency of the material can be further increased.

A separating device of a material of an absorbent article, wherein preferably a revolving direction of the shaft member and a rotating direction of the shaft member have a same rotation direction to each other.

With such a separating device of a material of an absorbent article, the protruding sections hit the material with a high-speed speed value formed by adding a speed value of revolving of the shaft member and a speed value of rotating of the shaft member. Thus, the hitting power to the material can be increased, and as a result the opening performance can be further improved.

A separating device of a material of an absorbent article, wherein preferably the protruding sections are sticklike members, a longitudinal direction of the sticklike member faces outward in a direction that intersects with an axial direction of the shaft member, and the sticklike member is arranged standing on a peripheral surface of the shaft member.

With such a separating device of a material of an absorbent article, because the protruding sections are sticklike members, a large surface area for hitting the material can be secured, and also between adjacent sticklike members, a space to take in the above material subject to be hit can be certainly secured. Then, in this way, the opening performance can be further improved.

A separating device of a material of an absorbent article, wherein preferably a space inside the case is divided into a first space and a second space with a partition member having a plurality of through holes, the insertion port and the discharge port are in communication with the first space, and the rotation member is housed inside the first space, the material has granular superabsorbent polymers as the impurities, the through holes of the partition member are formed with an opening size that regulates passing through of the liquid absorbent fibers and allows passing through of the super absorbent polymers, and the superabsorbent polymers that have passed through the through holes and that have entered into the second space pass a second discharge port provided in the second space and are discharged to outside of the case.

With such a separating device of a material of an absorbent article, with the above partition member, the liquid absorbent fiber can be stopped within the first space and the superabsorbent polymer can be selectively moved to the second space, thus the liquid absorbent fibers and the superabsorbent polymers can be quickly and certainly separated. Thus, purity of the liquid absorbent fibers to be discharged from the discharge port of the first space in the end can be improved.

Further, the superabsorbent polymers are discharged from the second discharge port of the second space, thus collection of the superabsorbent polymers can be easily and certainly performed.

A separating device of a material of an absorbent article, wherein preferably the second space is adjacent to below the first space, and the insertion port and the discharge port are provided in a ceiling section of the case, in a predetermined position between the insertion port and the discharge port in the first space, a regulating member that regulates movement of the material from the insertion port to the discharge port is suspended from the ceiling section.

With such a separating device of a material of an absorbent article, the holding time of the material in the first space can be extended and a long holding time can be ensured, thus the opening of the material can be progressed to a sufficient level. In other words, the opening performance can be further improved.

A separating device of a material of an absorbent article, wherein preferably the second space is provided with a suction port that suctions air inside the second space, liquid absorbent fibers that have passed the through holes of the partition member and float inside the second space are sucked in with the suction port.

With such a separating device of a material of an absorbent article, the liquid absorbent fibers that float in the second space are sucked in with the suction port, thus the collection rate of the liquid absorbent fiber can be increased.

A separating device of a material of an absorbent article, wherein preferably a part opposing the insertion port of the partition member is formed with perfect circular holes as the through holes, a part opposing the discharge port of the partition member is formed with holes having a large opening area than the circular holes and having a hole shape with a longitudinal direction and a transverse direction, as the through holes, the longitudinal direction of the holes faces a direction intersecting the revolving direction.

With such a separating device of a material of an absorbent article, in a position near the discharge port, the opening of the material has progressed sufficiently, and the material is in a state in which it can be easily separated into the liquid absorbent fibers and the superabsorbent polymers. The opening area of the through holes in the part opposing the discharge port in the partition member is set greater than the opening area of the circular holes in the part corresponding to the insertion port. Thus, based on the large opening area of the through holes, the superabsorbent polymers that are in the above-described state in which they can easily separate can be smoothly passed through and moved to the second space.

On the other hand, the longitudinal direction of the through holes is in a direction that intersects the revolving direction of the shaft member of the rotation member. Thus, the passing of the liquid absorbent fibers through the through holes can be effectively regulated and the fibers can be held in the first space. Then, as a result, the liquid absorbent fibers and the superabsorbent polymers can be smoothly separated.

Further, a separating method of separating liquid absorbent fibers from a material having the liquid absorbent fibers of an absorbent article and impurities, the method comprising:

inserting the material into the case from an insertion port, while the material is made to ride on an airflow;

agitating and opening the material with a rotation member housed inside the case; and discharging the liquid absorbent fibers, of the material that has been opened with the rotation member, from inside the case via a discharge port, while the liquid absorbent fibers are made to ride on an airflow, in the agitating and the opening of the material, using a shaft member as the rotation member, the shaft member being set with an axial direction along a predetermined direction from the insertion port to the discharge port, the shaft member having protruding sections that protrude outward in a direction that intersects with the axial direction, the shaft member rotating around a rotating axis that has been set with an axial direction along the predetermined direction, while revolving around the revolving axis that has been set along the predetermined direction.

With such a separating device of a material of an absorbent article, the rotation member has the shaft member having the protruding sections. Then, the shaft member rotates and revolves, and thus hits the material with the protruding sections, and agitates and opens the material. Thus, a high opening performance can be achieved, and as a result the separating performance of the liquid absorbent fibers from the material can be improved.

First Embodiment Mode

Figure 2A:
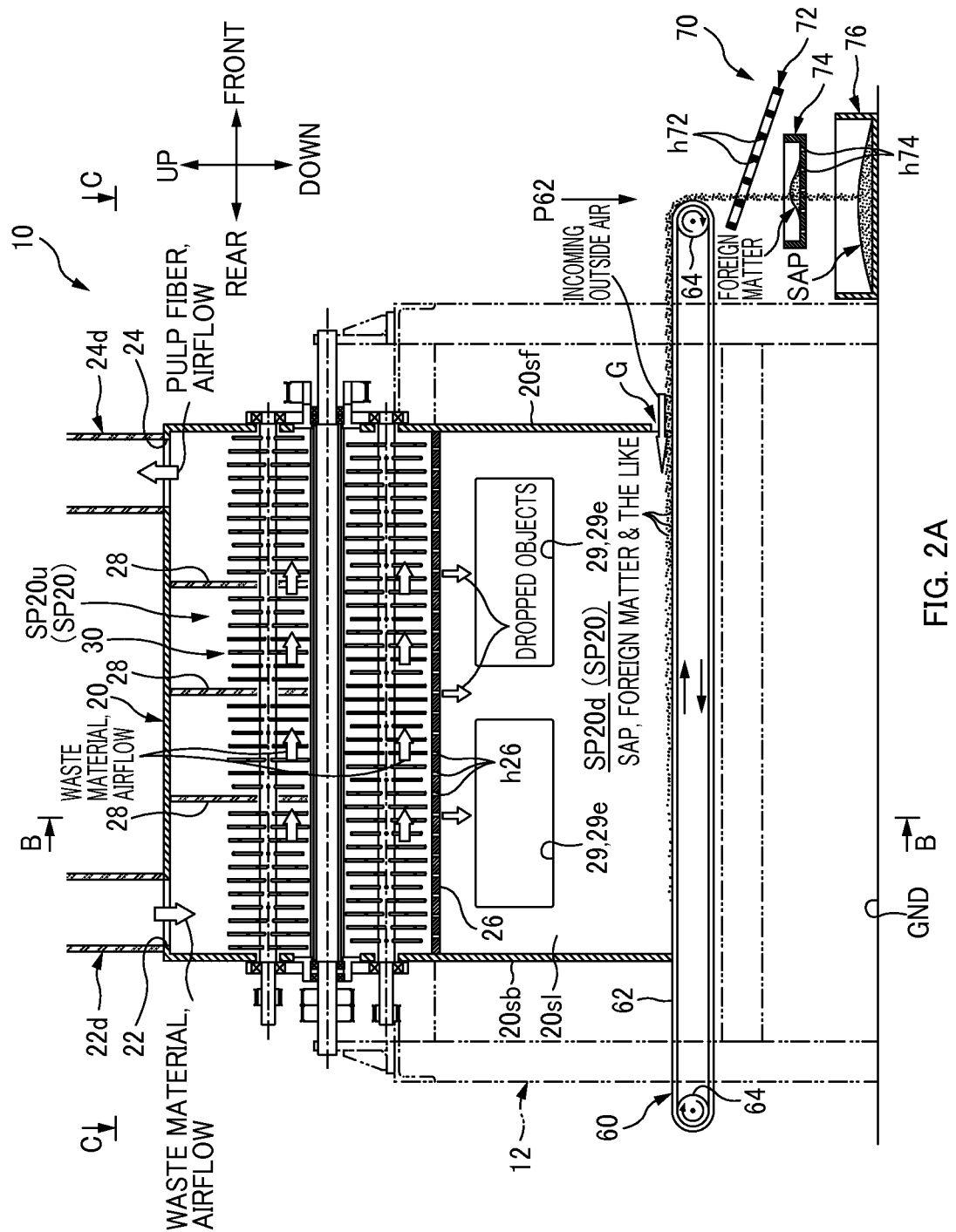
FIG. 2A, is a schematic vertical sectional view of a separating device 10 of a first embodiment mode.
Figure 2B:
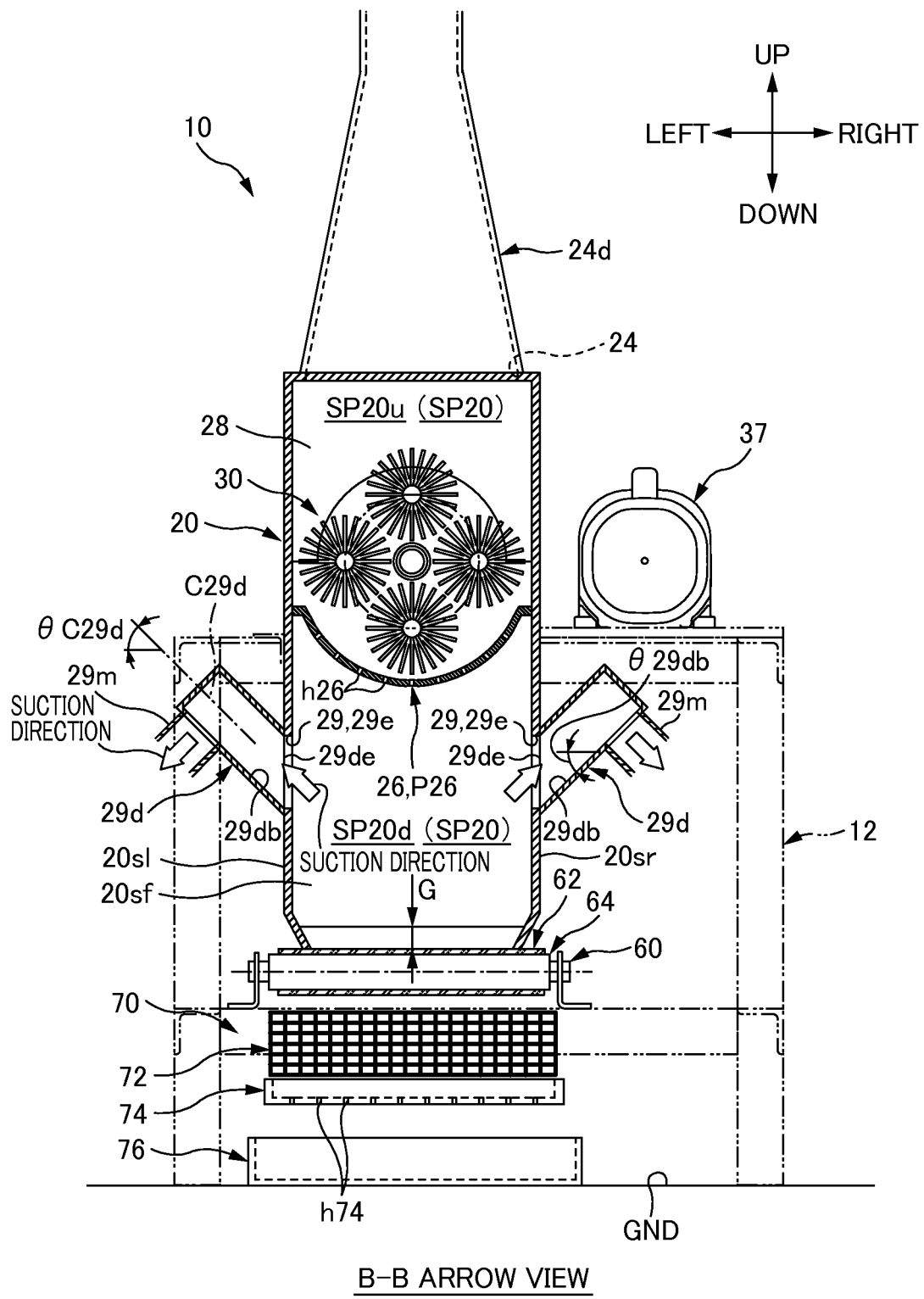
FIG. 2B is a B-B arrow view in FIG. 2A.
Figure 2C:
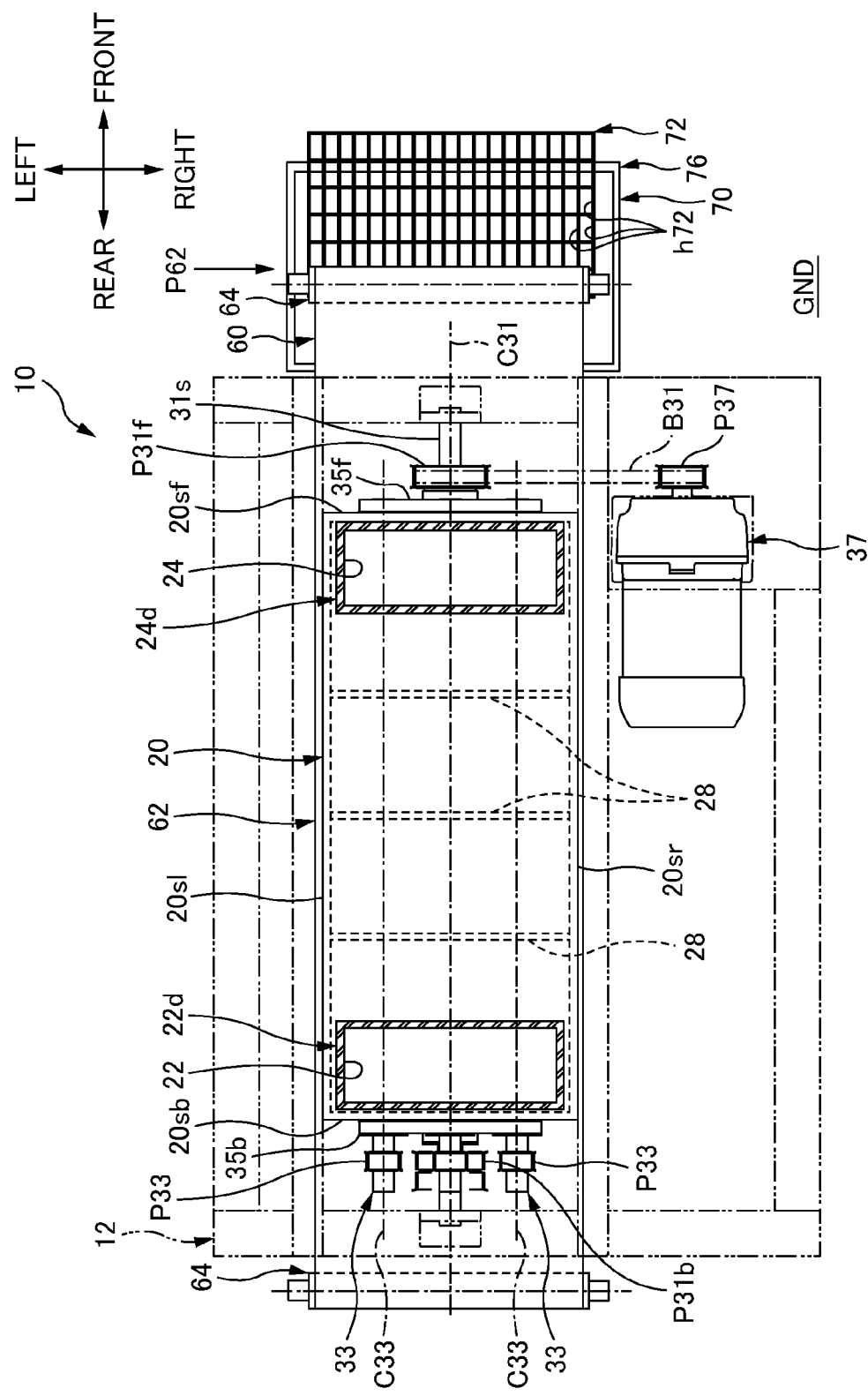
FIG. 2C is a C-C arrow view in FIG. 2A.

FIG. 2A and FIG. 2C are explanatory views of a separating device 10 of a first embodiment mode. FIG. 2A is a schematic vertical sectional view, FIG. 2B is a B-B arrow view in FIG. 2A, and FIG. 2C is a C-C arrow view in FIG. 2A. It should be noted that, in order to prevent mix up of the drawings, in all the drawing to be used hereafter including FIG. 2A to FIG. 2C, a sectional line that should be applied in reality to the sectional section is partially omitted in some cases.

This separating device 10 is inserted with waste material of an absorbent article as a material subject to be separated. The waste material has mainly, for example, an absorbent body of a disposable diaper. In other words, pulp fibers and particulate SAP that is mixed in the pulp fibers are the main materials of the waste material.

The absorbent body of the waste material is obtained by, for example, taking off from defective diapers made in a manufacturing process of disposable diapers such as leak prevention sheets made of a resin film, top sheets and back sheets made of nonwoven fabric, and rubber thread. In this case however, when taking off the above various sheets and the like from the diaper, for example, an applying part of a hot melt adhesive, a rubber thread and the like are mixed in the absorbent body in fragment forms as foreign matter. Thus, the separating device 10 separates the waste material into approximately three things, which are pulp fibers, SAP, and foreign matter. Namely, the pulp fibers are one example of "liquid absorbent fibers" according to the claims. Further, both the foreign matter and the SAP are examples of "impurities" of the claims, and hereafter these are referred to also as "impurities".

The separating device 10 has a case 20, an insertion port 22 that is formed as an opening in a ceiling section 20c of the case 20 and that is for inserting waste material into the case 20, while the material is made to ride on an airflow, a rotation member 30 housed in the case 20, the rotation member agitating and opening the waste material, a discharge port 24 for discharging mainly the pulp fibers, of the waste material that has been opened with the rotation member 30, from inside the case 20, while the pulp fibers are made to ride on an airflow, the discharge port being formed as an opening in the ceiling section 20c of the case 20, a dropped object discharge mechanism 60 arranged opposing a space SP20 in the case 20 in a lower position of the case 20, the dropped object discharge mechanism 60 discharging to the outside of the case 20 the dropped objects that drop in the case 20, and a separating member 70 that separates the dropped objects discharged to outside the case 20 with the dropped object discharge mechanism 60 into SAPs, foreign matter, and pulp fibers.

Here, as shown in FIG. 2A, an insertion port 22 and a discharge port 24 are each connected with the insertion duct 22d and the discharge duct 24d, and further the insertion duct 22d and the discharge duct 24d are each connected with an appropriate blower that is not shown. Then, an amount of air blown (m³/min) per unit time with the blower of the discharge duct 24d is set to be greater than an amount of air blown with the blower of the insertion duct 22d, and thus an airflow that flows basically from the insertion port 22 to the discharge port 24 is formed in a substantially upper half of the space SP20 in the case 20. Then, for example, the waste material is inserted from an open pipe end section (not shown) of the insertion duct 22d, this waste material rides on the above airflow and is sent from the insertion port 22 into the case 20, and then after being agitated and opened with the rotation member 30 inside the case 20, mainly the pulp fibers ride on the airflow and are discharged from the discharge port 24. Further, during this agitating and opening of the waste material, mainly the SAP and the foreign matter with greater specific gravity than the pulp fibers are dropped with its own weight and the like into the case 20 as dropped objects and received with a dropped object discharge mechanism 60, and then discharged to outside the case 20 with the same mechanism 60. It should be noted that, in the dropped objects are included the pulp fibers of a small amount other than the SAP and the foreign matter. Then, the discharged dropped objects are separated into pulp fibers, SAP, and foreign matter with the separating member 70.

Hereafter, each of the structures 20, 22, 24, 30, 60, 70 and the like are explained. It should be noted that, in the below description, three directions that are orthogonal with each other are referred to as an up-down direction, a front-rear direction, and a left-right direction. Namely, the up-down direction faces a vertical direction, and both the front-rear direction and the left-right direction face a horizontal direction.

Figure 3A:
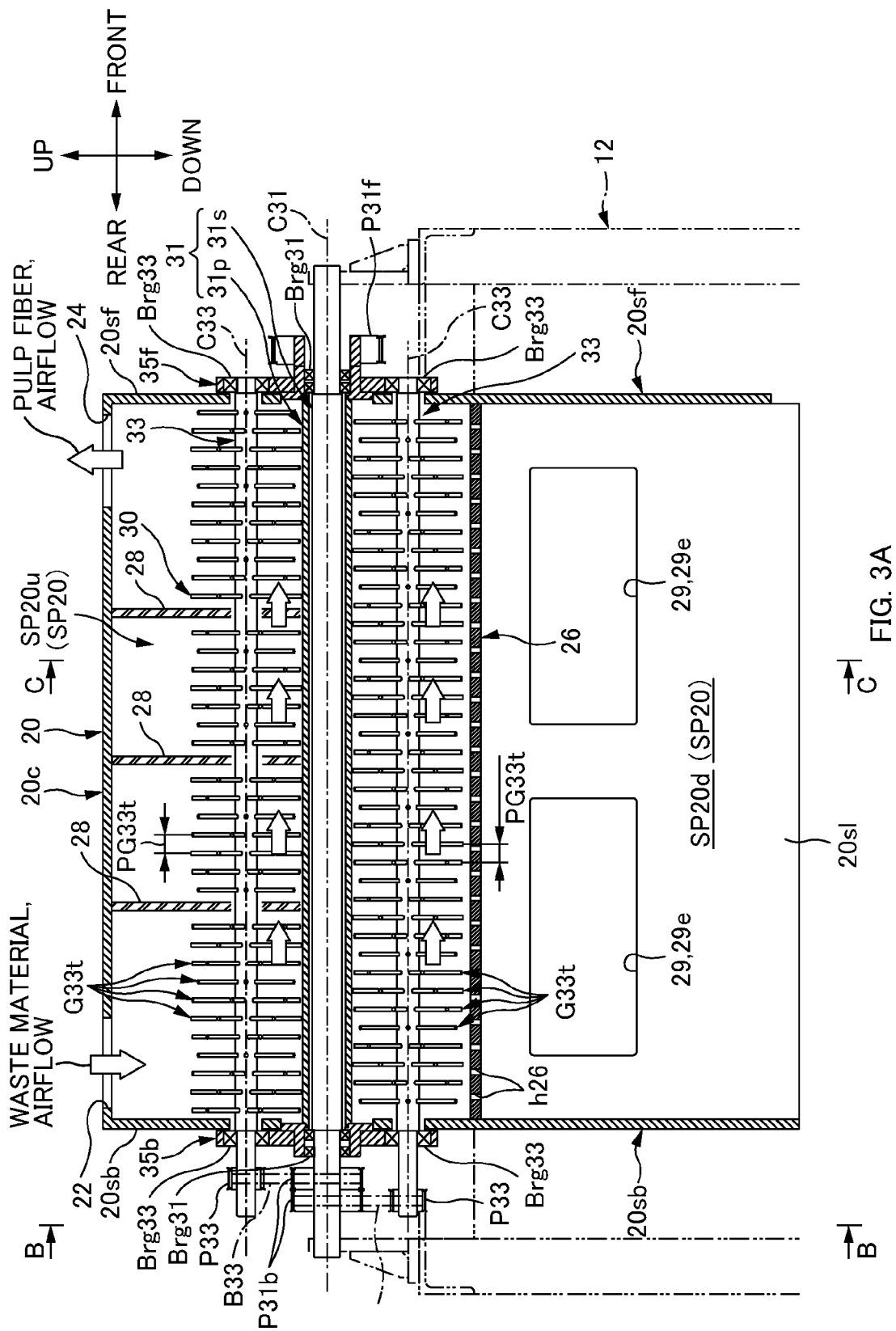
FIG. 3A is a schematic vertical sectional view showing mainly enlarged an upper half section of the separating device 10.
Figure 3B:
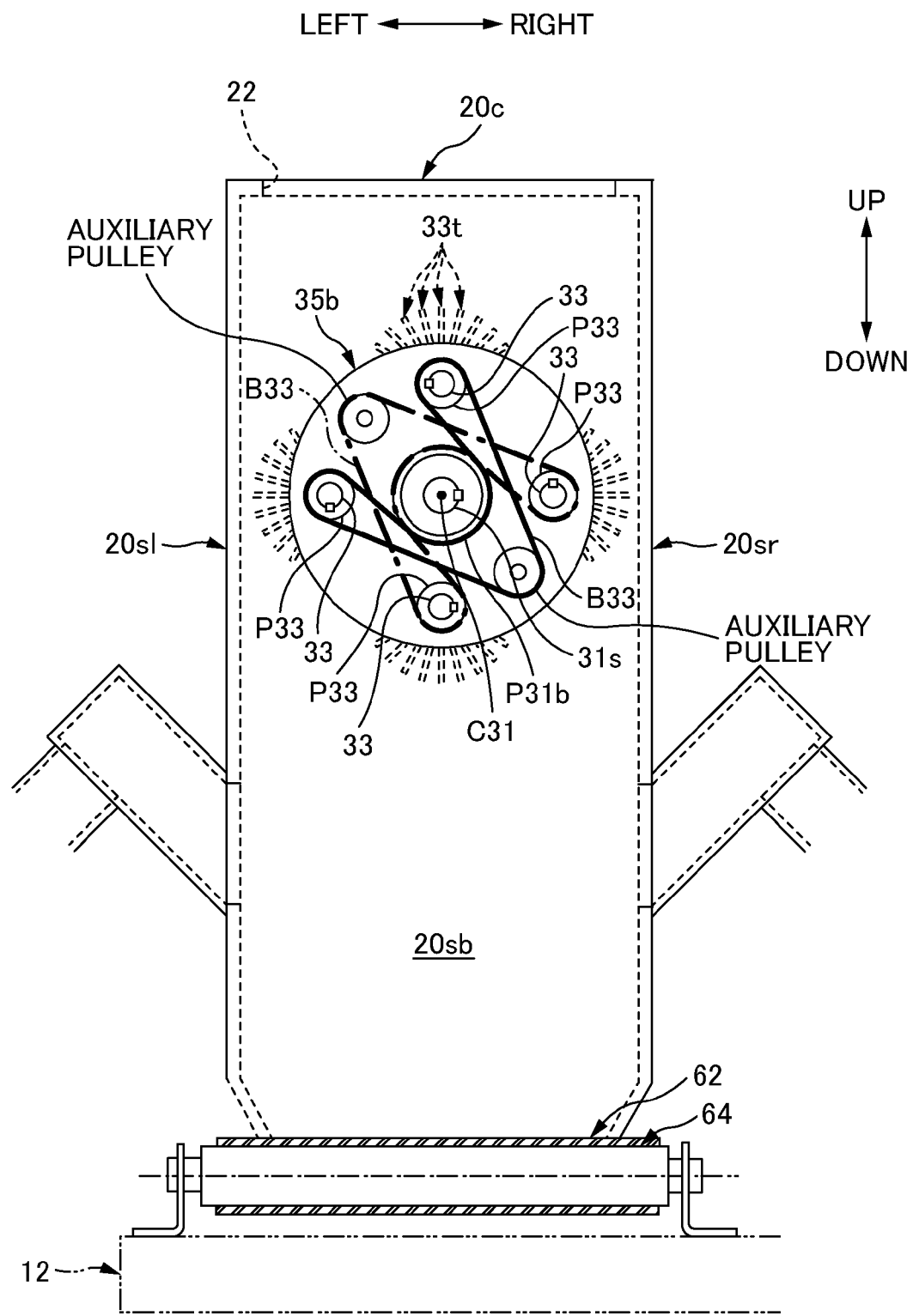
FIG. 3B is a B-B arrow view in FIG. 3A.
Figure 3C:
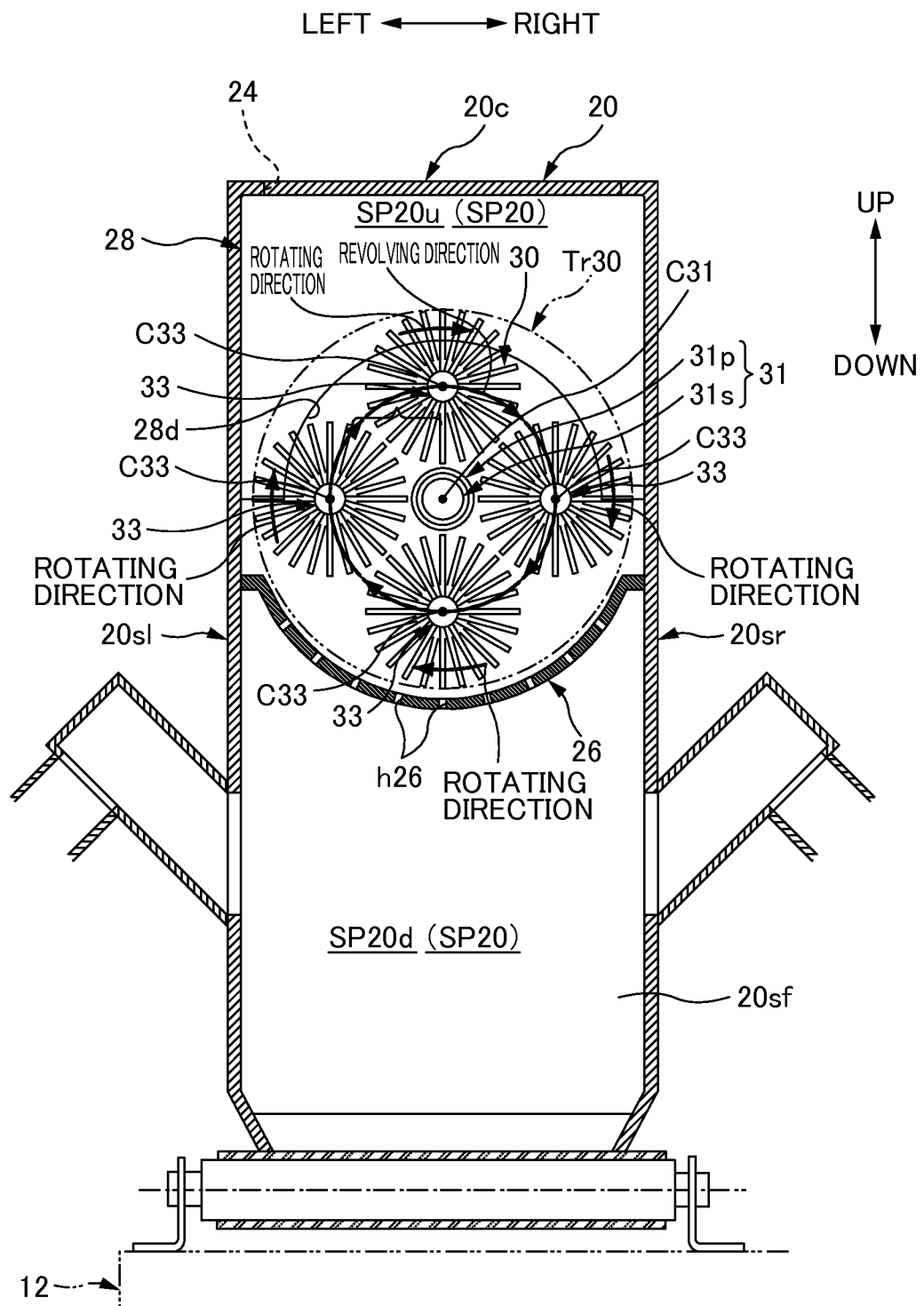
FIG. 3c is a C-C arrow view in FIG. 3A.

FIG. 3A is a schematic vertical sectional view showing mainly an enlarged upper half section of the separating device 10, FIG. 3B is a B-B arrow view in FIG. 3A, and FIG. 3C is a C-C arrow view in FIG. 3A.

<<Case 20, Insertion Port 22, Discharge Port 24>>

As shown in FIG. 3A to FIG. 3C, the case 20 is a bottomless box body without just a bottom surface section, and its exterior shape is a substantially rectangular parallelepiped shape. In other words, the case has a ceiling section 20c provided substantially horizontally, and four side wall sections 20sf, 20sb, 20sl, and 20sr. The side wall sections are each suspended from four sides to the front, rear, left, and right of the ceiling section 20c and from the four sides surround a space SP20 below the ceiling section 20c. It should be noted that, hereinbelow, a side wall section 20sf that suspends from a front edge section of the ceiling section 20c is referred to as a "front side wall section 20sf", and a side wall section 20sb that suspends from a rear edge section of the ceiling section 20c is referred to as a "rear side wall section 20sb", a side wall section 20sl that suspends from a left edge section of the ceiling section 20c is referred to as a "left side wall section 20sl", and a side wall section 20sr that suspends from a right edge section of the ceiling section 20c is referred to as a "right side wall section 20sr".

This case 20 is supported with an appropriate frame-like supporting member 12 fixed to a ground section GND of a factory, in a position with its longitudinal direction along the front-rear direction, and its transverse direction (width direction) along the left-right direction.

As shown in FIG. 3A, the insertion port 22 is formed open in a substantially rectangular shape in a rear end part in the ceiling section 20c, and on the other hand the discharge port 24 is formed open in a substantially rectangular shape in a front end part in the ceiling section 20c. In this way, the direction from the insertion port 22 to the discharge port 24 is set in parallel with the front-rear direction.

Further, as shown in FIG. 3A and FIG. 3C, inside the case 20 is provided a partition board 26 (corresponds to a partition member). With this partition board 26, the space SP20 inside the case 20 is divided into an upper space SP20u (corresponds to a first space) and a lower space SP20d (corresponds to a second space) adjacent to below the upper space SP20u. The upper space SP20u houses a rotation member 30. Further, the partition board 26 is formed with a plurality of through holes h26, h26 . . . that are in communication with the upper space SP20u and the lower space SP20d, and further, the opening size of these through holes h26 allow impurities (in other words, the SAP and the foreign matter) in the waste material to pass through, and are set to an opening size that restricts passing through of pulp fibers. Thus, in the process the waste material is opened with the rotation member 30, the impurities such as the SAP and the foreign matter that are in a state detachable from the pulp fibers pass through the through holes h26 swiftly and drop into the lower space SP20d as dropped objects, but on the contrary the pulp fibers are effectively held in the upper space SP20u, thereafter these pulp fibers are simply discharged from the discharge port 24 of the ceiling section 20c.

<<<Rotation Axis Member 30>>>

As shown in FIG. 3A and FIG. 3C, the rotation member 30 has a revolving axis C31 set with an axial direction along and in parallel with the front-rear direction, and a plurality of shaft members 33, 33 . . . that rotate around rotating axes C33 set with the axial direction along and in parallel with the front-rear direction, while revolving around the revolving axis C31.

The revolving axis C31 is realized with a revolving axis forming shaft member 31 arranged with the axial direction along and in parallel with the front-rear direction. The revolving axis forming shaft member 31 has an outer pipe 31p arranged with a pipe axis direction in parallel with the front-rear direction, and an inner shaft 31s that is passed through substantially concentrically inward of the outer pipe 31p. The inner shaft 31s is supported in both ends with the frame-like supporting member 12 mentioned above so that it cannot move relatively, and on the other hand the outer pipe 31p is supported with the inner shaft 31s relatively rotatably around the axial core of the inner shaft 31s via a bearing Brg31. Further, the front end section in the front-rear direction of the outer pipe 31p is fixed with a circular flange board 35f via an appropriate connecting structure relatively non-movably and substantially concentrically, and this flange board 35f is provided to come in contact with the front side wall section 20sf of the case 20 from the front in an adjacent manner. Similarly, the rear end section of this outer pipe 31p is fixed with the circular flange board 35f relatively non-movably and substantially concentrically via an appropriate connecting structure, and the flange board 35b is provided adjacently so as to come in contact from the rear to the rear side wall section 20sb of the case 20. Then, this pair of flange boards 35f, 35b supports both ends of each of the shaft members 33, 33 . . . rotatably via bearings Brg33 in a state that the axial direction is facing in parallel with the front-rear direction.

On the other hand, the above flange board 35f positioned in the front end section of the outer pipe 31p is fixed with a pulley P31f, and this pulley P31f is to be input with a rotation operation via an endless belt B31 (FIG. 2C) from a pulley P37 of an electric motor 37 as a drive source. Further, as shown in FIG. 3A and FIG. 3B, from the above flange board 35b positioned in the rear end section of the outer pipe 31p, the rear end section of each of the shaft members 33 is protruded to the rear, and each rear end section is fixed with the pulley P33, and further a pulley P31b is fixed to the inner shaft 31s corresponding to these pulleys P33. Then, an endless belt B33 is put around the corresponding pulleys P33 and P31b.

Thus, when the electric motor 37 is activated, the outer pipe 31p and the pair of the flange boards 35f, 35b integrally rotate, and accompanying this, each of the shaft members 33, 33 . . . supported with the pair of the flange boards 35f, 35b are applied a rotating force from this pair of the flange boards 35f, 35b, and revolve around the revolving axis C31 which moves around the outer pipe 31p. Then, at this time, the endless belt B33 is put around both the pulley P33 and the pulley P31b, and thus with the revolution of each of the shaft members 33, each of the shaft members 33 rotates for the amount of change of the revolving position. Thus, using one electric motor 37 as the drive source, the rotating operation and the revolving operation of each of the shaft members 33 is performed.

Figure 4:
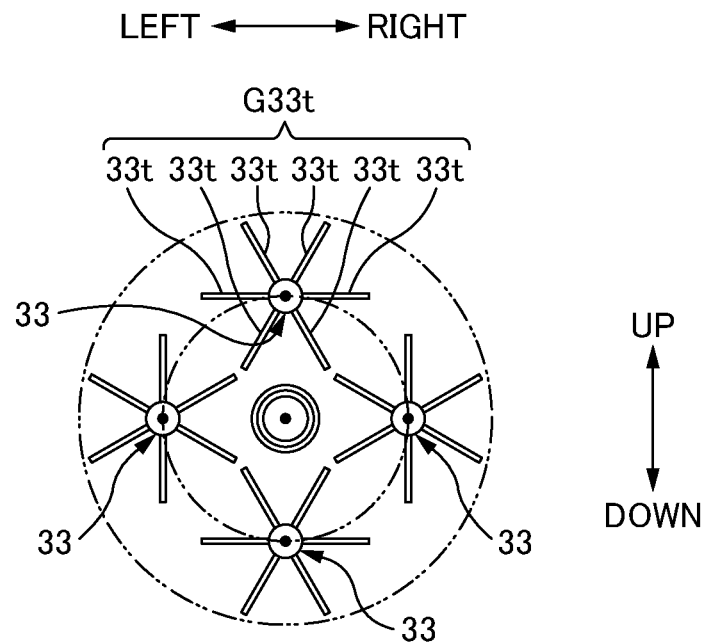
FIG. 4 is a view of one protrusion section group G33t of a shaft member 33 seen from a front-rear direction.

By the way, in this example, as shown in FIG. 3C, four shaft members 33, 33 . . . as an example of a plurality of members, are provided lined in 90 degrees intervals of an equal pitch in the revolving direction. Further, each of the shaft members 33 has a protruding section group G33t with a plurality of protruding sections 33t, 33t . . . such as shown in FIG. 4 arranged radially in 60 degrees intervals of an equal pitch in the rotating direction. Then, the protruding section group G33t is, as shown in FIG. 3A, provided in a predetermined pitch in a plurality of positions in the axial direction of the shaft member 33. Thus, a hitting frequency of the waste material with the protruding sections 33t can be increased, and high opening performance can be performed.

Further, in this example, each of the protruding sections 33t is configured with stick-like members 33t with the same length as each other arranged standing on the peripheral surface of the shaft member 33, and in more detail, a steel round bar with a circular cross section is used as the stick-like member 33t, and further, its longitudinal direction is facing outward in an intersecting direction of the axial direction of the shaft member 33. The waste material is hit with the peripheral surface of the stick-like member 33t. Thus, the surface area that hits the waste material can be largely secured. Further, with the stick-like member 33t, a space to take in the waste material can be largely secured in between the adjacent stick-like members 33t, 33t. However, the stick-like member 33t is not limited to the above steel round bar in any way, and may be, for example, a steel square bar with a rectangular cross section, or may be a non-ferrous round bar. Further, the protruding section 33*t* does not have to be configured as the stick-like member 33*t*, and for example, may be configured as a plate-like member. However, with the stick-like member 33*t*, a larger space can be secured to take in the waste material as described above, and thus is more preferable than the plate-like member.

Further, in this example, the longitudinal direction of the stick-like member 33*t* is orthogonal to the axial direction of the shaft member 33, but it is not limited thereto in any way. In other words, even if the directions are not orthogonal but intersect with each other, a reasonable hitting performance can be performed.

Further, as can be seen from a comparison between FIG. 4 and FIG. 3C, or from FIG. 3A, preferably, the protruding section groups G33*t*, G33*t* that are adjacent to each other in the axial direction of the shaft member 33, the arrangement positions of the protruding sections 33*t* to each other are shifted in the rotating direction. In this example, with respect to the protruding section group G33*t* that is a predetermined standard, the arrangement positions of the protruding sections 33*t* of the protruding section group G33*t* positioned adjacent thereof is shifted in the rotating direction by 15 degrees, and further, the protruding section group G33*t* positioned adjacent thereof is further shifted with a same shifting amount of 15 degrees in the same direction, and this shifting operation is performed repeatedly with respect to all the protruding section groups G33*t*, G33*t* . . . lined in the axial direction.

Then, when configured in this way, immediately after the protruding sections 33*t* belonging to the predetermined protruding section group G33*t* hit the waste material, the protruding sections 33*t* belonging to the protruding section group G33*t* positioned adjacent in the axial direction can hit again this waste material, and as a result the hitting frequency of the waste material can be increased.

Namely, as described above in reference to FIG. 4, each of the protruding section groups G33*t* has the protruding sections 33*t* in 60 degrees intervals in the rotating direction, thus with the above described shifting operation of 15 degrees, the protruding section group G33*t* with the same arrangement positions of the protruding sections 33*t* appears for every three sections (in other words, in a ratio of one to four) as shown in FIG. 3A.

The shifting amount, however, is not limited to the above 15 degrees in any way, and may be an arbitrary angle, and further, does not have to be shifted with the same shifting amount in the same direction regularly as described above, and for example, one or both of the shifting direction and the shifting amount may be random.

Further, preferably, as shown in FIG. 3A, regarding the shaft members 33, 33 adjacent to each other in the revolving direction, the arrangement positions of the protruding section groups G33*t* to each other may be shifted in the axial direction to each other. In this example, the shaft members 33, 33 that are adjacent to each other are both provided with the protruding section groups G33*t*, G33*t* . . . with a same pitch PG33*t* in the axial direction, and due to this, the adjacent shaft members 33, 33 are arranged alternately to each other so that the protruding section group G33*t* of the shaft member itself is positioned in a middle position between the protruding section group G33*t* belonging to the other shaft member 33 and the protruding section group 33*t* adjacent thereof in the axial direction.

Then, with a configuration as described above, immediately after the protruding sections 33*t* of the protruding section group G33*t* of the predetermined shaft member 33 hit the waste material, the protruding sections 33*t* of the protruding section group G33*t* of the shaft member 33 positioned adjacent in the revolving direction can again hit the waste material, and this also contributes effectively in the increase of the hitting frequency of the waste material described above.

In other words, in FIG. 3A, it is difficult to show both the adjacent shaft members 33, 33, and thus for the sake of convenience, the positions of the protruding section groups G33*t* are shown to be alternate between the shaft member 33 positioned above and the shaft member 33 positioned below, but in reality both the two upper and lower shaft members 33, 33 shown in FIG. 3A are in an adjacent positional relationship to each other in the revolving direction. In other words, the shaft members are in an adjacent positional relationship with a 90 degrees interval in the revolving direction.

Further, preferably, as shown in FIG. 3C, between the revolving direction of the shaft member 33 and the rotating direction of the shaft member 33, the rotation directions of each other are the same. For example, in the case that the revolving direction is a clockwise direction, corresponding to this, the rotating direction is also made clockwise. On the contrary, in the case that the revolving direction is counterclockwise, the rotating direction may also be counterclockwise. Thus, in this way, with a high speed value that is formed by adding a speed value of revolution of the shaft member 33 and a speed value of rotating on its own axis of the shaft member 33*t*, the protruding sections 33*t* hit the waste material. Thus, the hitting force to the waste material can be increased, and this also contributes to improvement of the opening performance.

Figure 5:
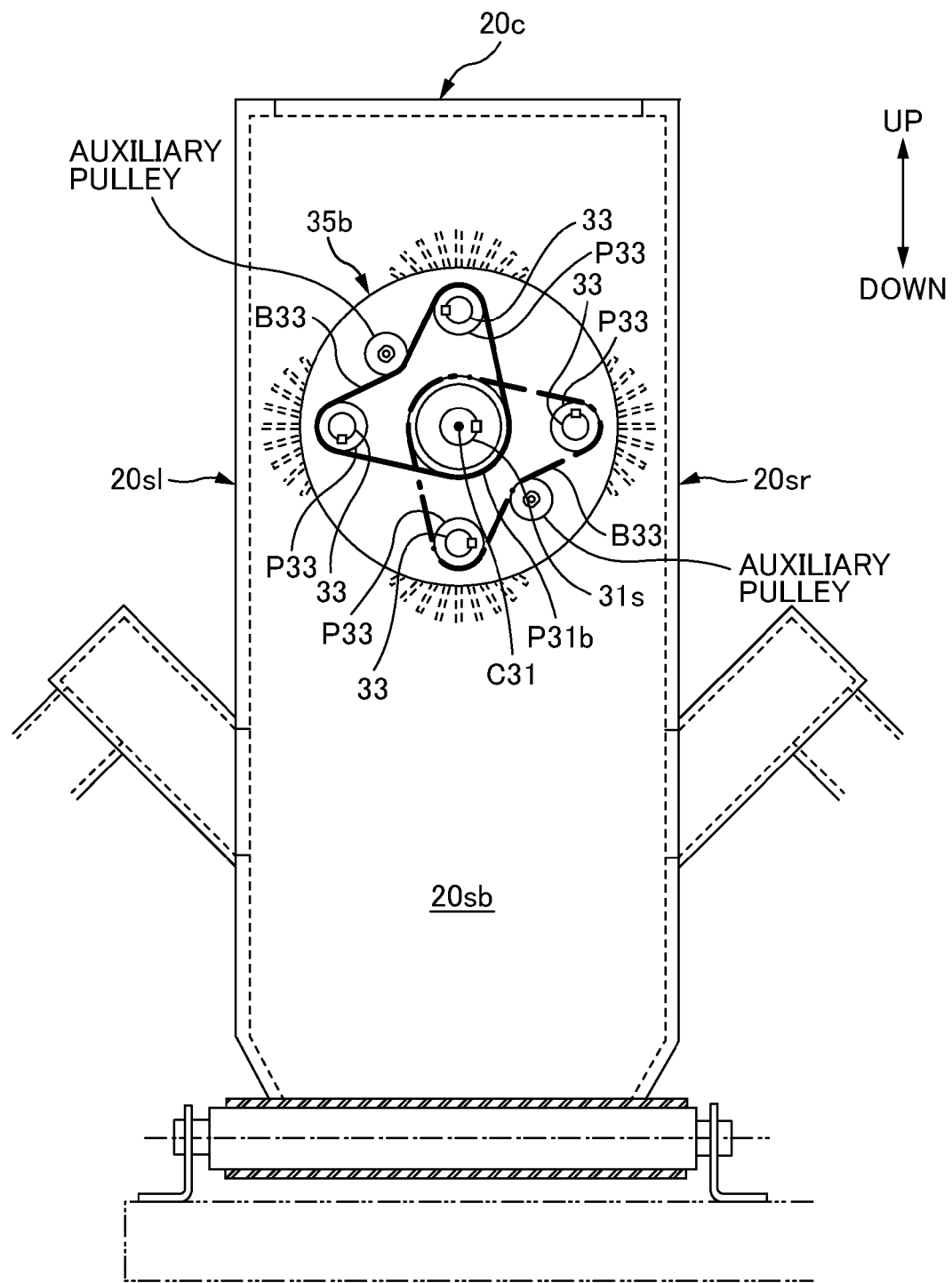
FIG. 5 is a diagram showing an example of how to put around an endless belt B33 in the case where, between a revolving direction and a rotating direction of the shaft member 33, the rotation directions of each other are made to be in opposite directions.

It should be noted that, to align the rotation directions of each other to a same direction as described above is realized by devising a way to put the endless belt B33 around the pulleys P33, P31*b* as in FIG. 3B. In other words, as shown in FIG. 3B, in the case that the endless belt B33 is put around so that one pulley of either the pulley P33 of the shaft member 33 or the pulley P31*b* of the inner shaft 31*s* is made to come into contact with an inner peripheral surface of the endless belt B33, and the other pulley is made to come in contact with an outer peripheral surface of the endless belt B33, unifying of the above rotation directions will be realized. In other words, in the case that supposedly between the revolving direction of the shaft member 33 and the rotating direction of the shaft member 33, the rotation directions to each other are to be reversed, as shown in FIG. 5, the endless belt may be put around so that both the pulley P33 of the shaft member 33 and the pulley P31*b* of the inner shaft 31*s* come into contact with the inner peripheral surface of the endless belt B33.

By the way, as shown in FIG. 3A and FIG. 3C, as described above, inside the case 20, the partition board 26 with through holes h26, h26 . . . is provided near to below the rotation member 30, and this partition board 26 is bent in an arc shape protruded below as shown in FIG. 3C. Thus, the partition board is provided along a rotation path Tr30 of the rotation member 30, namely along a rotation path Tr30 drawn with a tip end section of the protruding section 33*t* with the revolving and rotating of the shaft member 33, and as a result, a distance with respect to this rotation path Tr30 can be maintained substantially constantly over the entire length in the arc direction.

Further, various specifications such as an opening shape, an opening area, and the arrangement pattern of the through holes h26 formed in the partition board 26 are decided according to the position in the front-rear direction. Thus, in this example, two types of partition boards 26 with specifications of the through holes h26 different from each other are prepared as one example of a plurality of kinds of examples.

For example, as shown in FIG. 3A, an unopened block or granular waste material, riding on the airflow facing downward from the insertion port 22, reaches the partition board 26 provided in a rear position opposing the insertion port 22. Thus, in this rear position, for the purpose of certainly catching this waste material, there is provided a partition board 26 with a small opening ratio of the through holes h26 (a ratio of an area of the through holes h26 that occupy a plate surface of the partition plate 26 (includes the area of the through holes h26)), and that is set with a small opening area of each of the through holes h26. Specifically, in consideration that such as the granular diameter of the SAP is 150 to 850 μm, the partition board 26 formed with a plurality of circular holes with a diameter of 5 mm±1 mm with an opening ratio of 40 to 50% and in a staggered arrangement is used. In other words, a lower limit value of the above diameter is decided from the viewpoint of preventing clogging.

On the contrary, in a front position in which the discharge port 24 opposes, opening of the waste material with the rotation member 30 is progressed sufficiently, thus it is easy to separate the SAP and the foreign matter from the pulp fibers of the waste material, and further, the pulp fibers are not in a block or granular state and are sufficiently loosened to a string-state, and this pulp fiber tends to easily rise with the airflow.

Thus, even if the opening ratio and the opening area are made slightly large for the through holes h26 of the partition board 26 provided in this front position, passing through of the pulp fibers are suppressed, thus to facilitate passing through of the SAP and the foreign matter blown to the partition board 26 by springing off from the sticklike members 33t of the rotation member 30, the opening ratio of the through holes 26 are set larger than the partition board 26 in the rear position described above, and the opening area of the through holes h26 are set larger than the round holes of the partition board 26 in the rear position.

Figure 6A:
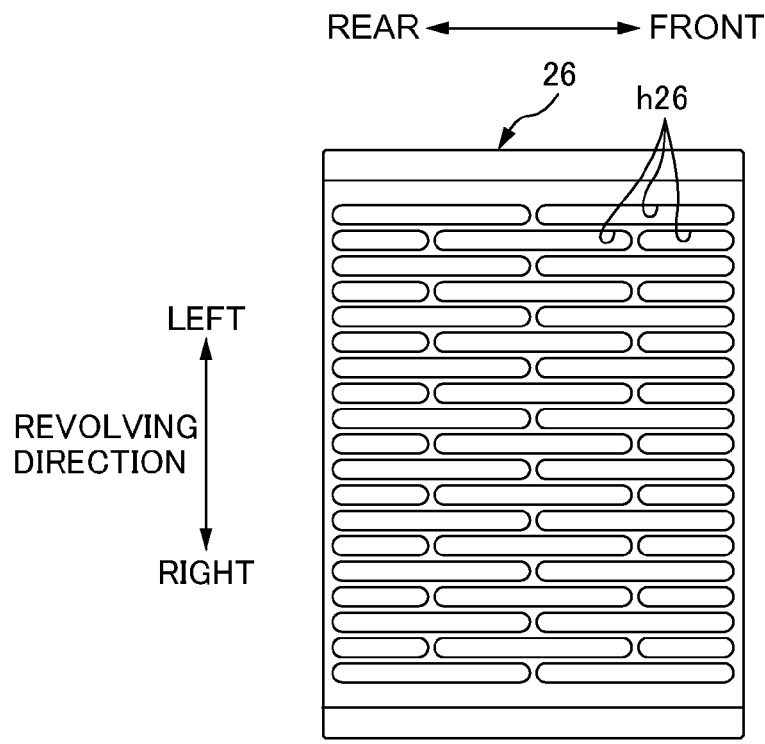
FIG. 6A is a schematic developed view of a sectional arc-shaped partition board 26 arranged in each of a front position and an intermediate position in a space SP20 inside the case 20.

Further, in order for the pulp fibers loosened to a string-like state to be easily caught in the through holes h26, the shape of the through holes h26 is set as long holes having a longitudinal direction and a transverse direction (width direction) as shown in a substantially developed view of FIG. 6A, and the longitudinal direction of the through holes h26 is in a direction intersecting the revolving direction of the rotation member 30 (to be accurate, a direction formed by projecting the revolving direction on a board surface of the partition board 26). Specifically, this partition board 26 is formed with long holes having a length 30 to 155 mm×a width 5 to 35 mm and having a size in which the length is greater than the width, the long holes having an opening ratio of 50% to 65%, the opening ratio being greater than the opening ratio of the partition board 26 in the above rear position, the holes being in a staggered arrangement with the longitudinal direction being orthogonal to the revolving direction.

Figure 6B:
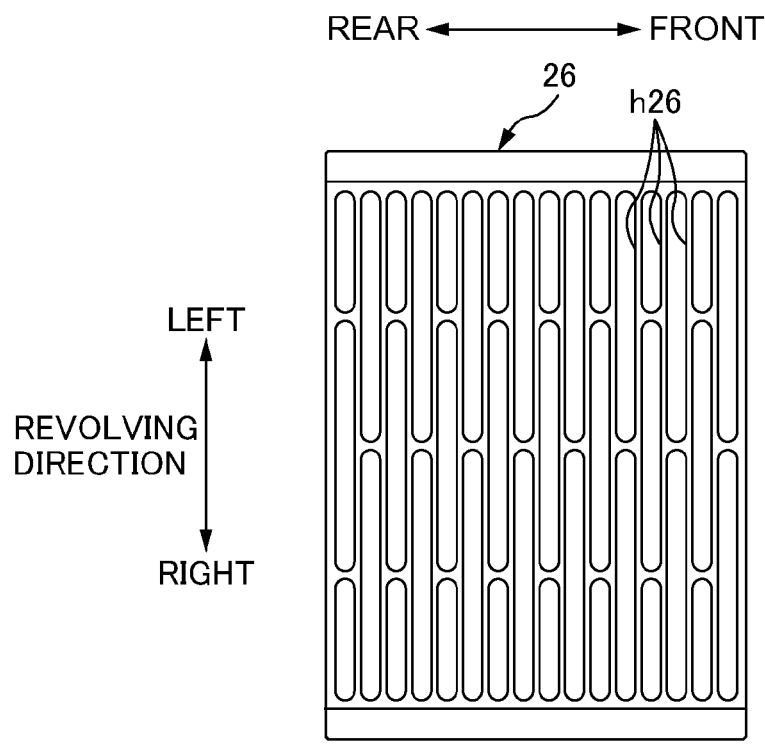
FIG. 6B is schematic developed view of a sectional arc-shaped partition board 26 having a long hole as a through hole h26 that has a longitudinal direction that is in parallel with the revolving direction.

In other words, as shown in the substantially developed view in FIG. 6B, the reason that the pulp fibers become easy to pass through the long holes, in the case that the longitudinal direction of the long holes which are the through holes h26 do not intersect the revolving direction (to be accurate, a direction formed by projecting the revolving direction on the board surface of the partition board 26), in other words, in the case that the longitudinal direction of the long holes are in parallel with the revolving direction, is considered to be as follows. First, the pulp fibers that have been sufficiently opened are loosened and are in a string-like state, so that compared to the case of being in a block or a granular state, it is difficult for the pulp fibers to pass through the long holes which are the through holes 26. In such a case, however, in the case that the longitudinal direction of the long holes are in parallel with the revolving direction, the pulp fibers which have a tendency to flow in the revolving direction with the revolution of the rotation member 30 have a long time facing the long holes, and as a result easily pass the long holes. In other words, when the longitudinal direction of the long holes are made to be in parallel with the revolving direction, the size of the long holes in the direction in parallel with the revolving direction becomes large, and the pulp fibers become easy to pass the long holes.

The shape of the through holes h26, however, are not limited in any way to the long holes with the longitudinal direction in parallel with the front-rear direction such as shown in FIG. 6A. In other words, in some cases, the shape of the through holes h26 may be long holes with the longitudinal direction in parallel with the left-right direction (revolving direction) as in FIG. 6B described above, or may have an opening shape with a square hole, or further may have an opening shape with holes of a polygon-shape or a round hole other than a rectangle.

Further, in this example, the partition board 26 is formed as a size with an entire length of the case 20 in the front-rear direction divided into three. The partition board 26 with the former round holes is arranged in the rear position, and both the middle position, between the front position and the rear position, and the front position are arranged each with the partition board 26 with the latter long holes. The arrangement pattern of the partition board 26 however, is not limited to this in any way.

<<Dropped Object Discharge Mechanism 60, Separating Member 70>>

As shown in FIG. 2A and FIG. 2C, the dropped object discharge mechanism 60 has a belt conveyor supported with the above described frame-like supporting member 12 as a main body. In other words, the dropped object discharge mechanism 60 has an endless belt 62 with an upper surface as a transporting surface, a plurality of rollers 64, 64 that is wrapped around with the endless belt 62 and that defines a circulating path of the endless belt 62. At least one of these rollers 64, 64, is a drive roller that is driven and rotated with a power motor as a driving source, and the endless belt 62 circulates with the drive roller.

Here, the upper surface which is the transporting surface of the endless belt 62, is set substantially as a horizontal surface, and the upper surface is positioned to oppose a lower end opening (corresponds to a second discharge port) of the case 20 and to cover the entire surface of the lower end opening from below. Thus, the endless belt 62 can certainly receive objects that fall in a lower space SP20d of the case 20 as dropped objects. Further, the movement direction of the upper surface of the endless belt 62 is to the front in the front-rear direction. Then, in a position to the front side than the case 20, in other words, in a position to the front than the front side wall section 20sf, is set a turning position P62 in which the movement direction of the endless belt 62 is turned. Thus, the dropped objects that have been received on the upper surface of the endless belt 62, is dropped from the endless belt 62 in the turning position P62 to the front. Then, the objects dropped from the endless belt 62 are separated into three of pulp fibers, SAPs, and the foreign matter, with the separating member 70 arranged below this turning position P62.

As shown in FIG. 2A and FIG. 2C, the separating member 70 has a first sieve member 72, a second sieve member 74 arranged below the first sieve member 72, and a lidless container 76 arranged below the second sieve member 74. Then, the first sieve member 72 has a plurality of through holes h72, h72, . . . and the opening size of the through holes h72 is set to an opening size that allows the SAPs and the foreign matter to pass through, and to regulate passing through of the pulp fibers. For example, the first sieve member 72 is configured of a wire gauze, and the wire gauze has as the through holes h72 rectangular openings with a vertical size of 20 to 30 mm×a horizontal size of 20 to 30 mm. Thus, the pulp fibers are selectively caught with the first sieve member 72. By the way, in the case that the opening is set to less than 20 mm, the foreign matter is caught in the wire gauze and is easier to enter the pulp fiber side, and on the other hand, in the case that the opening is set to greater than 30 mm, it becomes difficult for the pulp fibers to get caught in the wire gauze and separating becomes difficult.

Further, the second sieve member 74 also has a plurality of through holes h74, and the opening size of the through holes h74 is set to an opening size to allow the SAPs to pass through and to regulate passing through of the foreign matter. For example, the second sieve member 74 is also configured of a wire gauze, and the wire gauze has as the through holes h74 rectangular openings with a vertical size of 1.5 to 2 mm×a horizontal size of 1.5 to 2 mm. Thus, the foreign matter is selectively caught with the second sieve member 74. By the way, in the case that the opening is set to smaller than 1.5 mm, the SAPs do not pass through the through holes h74 smoothly and are caught with the wire gauze and tends to accumulate. On the other hand, in the case that the opening is set to greater than 2 mm, it becomes difficult for the foreign matter to get caught in the wire gauze and will enter the SAP side and separation becomes difficult.

It should be noted that, preferably, as shown in FIG. 2A and FIG. 2B, a gap G is provided between a lower end edge section of the front side wall section 20sf and an upper surface of the endless belt 62, and on the other hand, a gap is not provided between each of the lower end edge sections of the rear side wall section 20sb, the left side wall section 20sl, and the right side wall section 20sr, and the upper surface of the endless belt 62 and they are made to come into contact with each other. In other words, these lower end edge sections may be made to slide on the upper surface of the endless belt 62. In this way, based on such as a difference in an airflow amount between the above described insertion port 22 and the discharge port 24, the space SP20 (SP20d) in the case 20 is maintained in a negative pressure state with a lower atmospheric pressure than the outside, thus outside air enters in the lower space SP20d from the above gap G, and this incoming outside air also contributes to separation of the SAPs and the foreign matter and the pulp fibers from the dropped object.

Figure 7A:
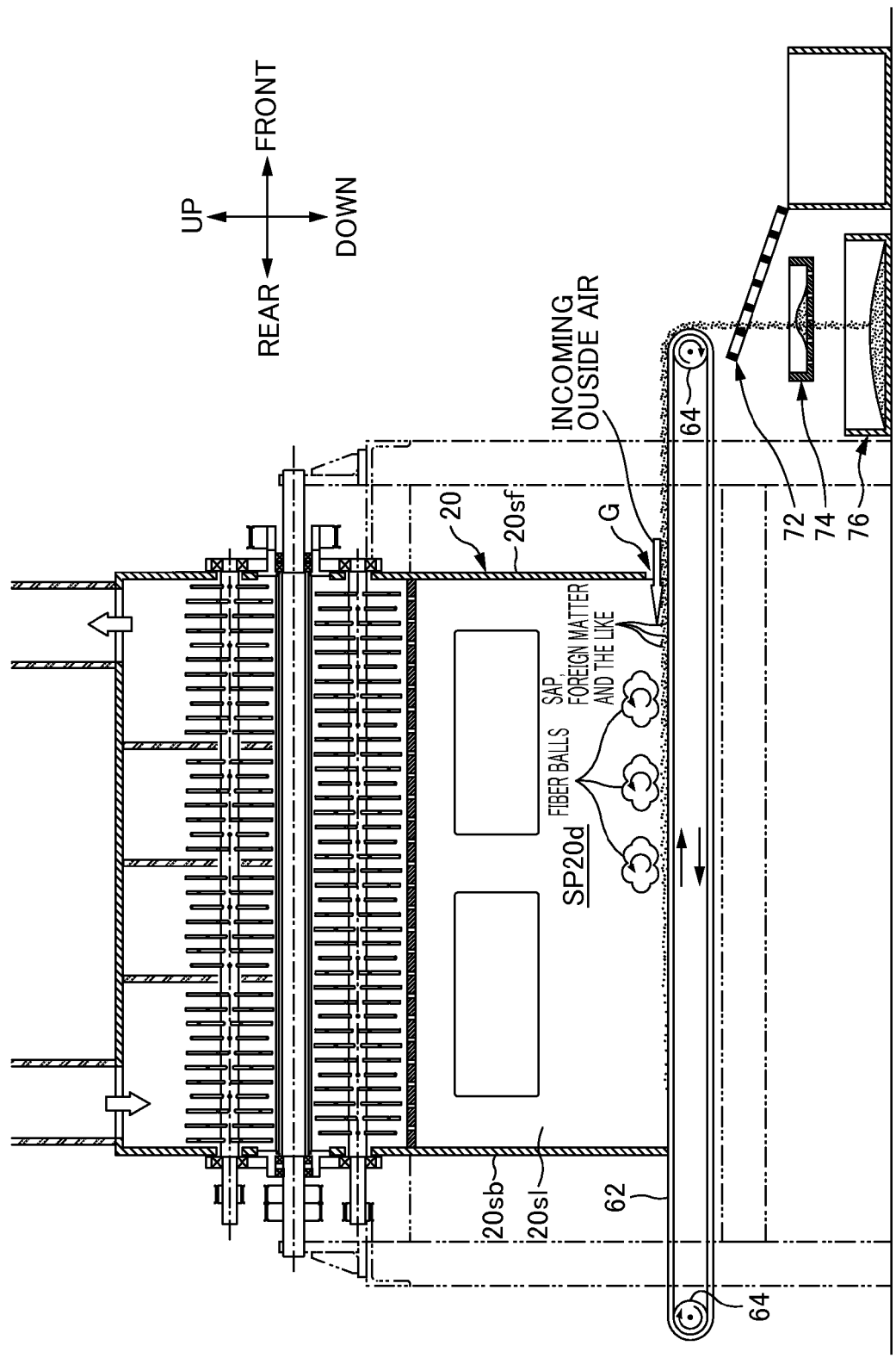
FIG. 7A is a schematic vertical sectional view showing a manner in which an incoming outside air from a gap G of the case 20 separates dropped articles into either SAP and foreign matter or pulp fibers.
Figure 7B:
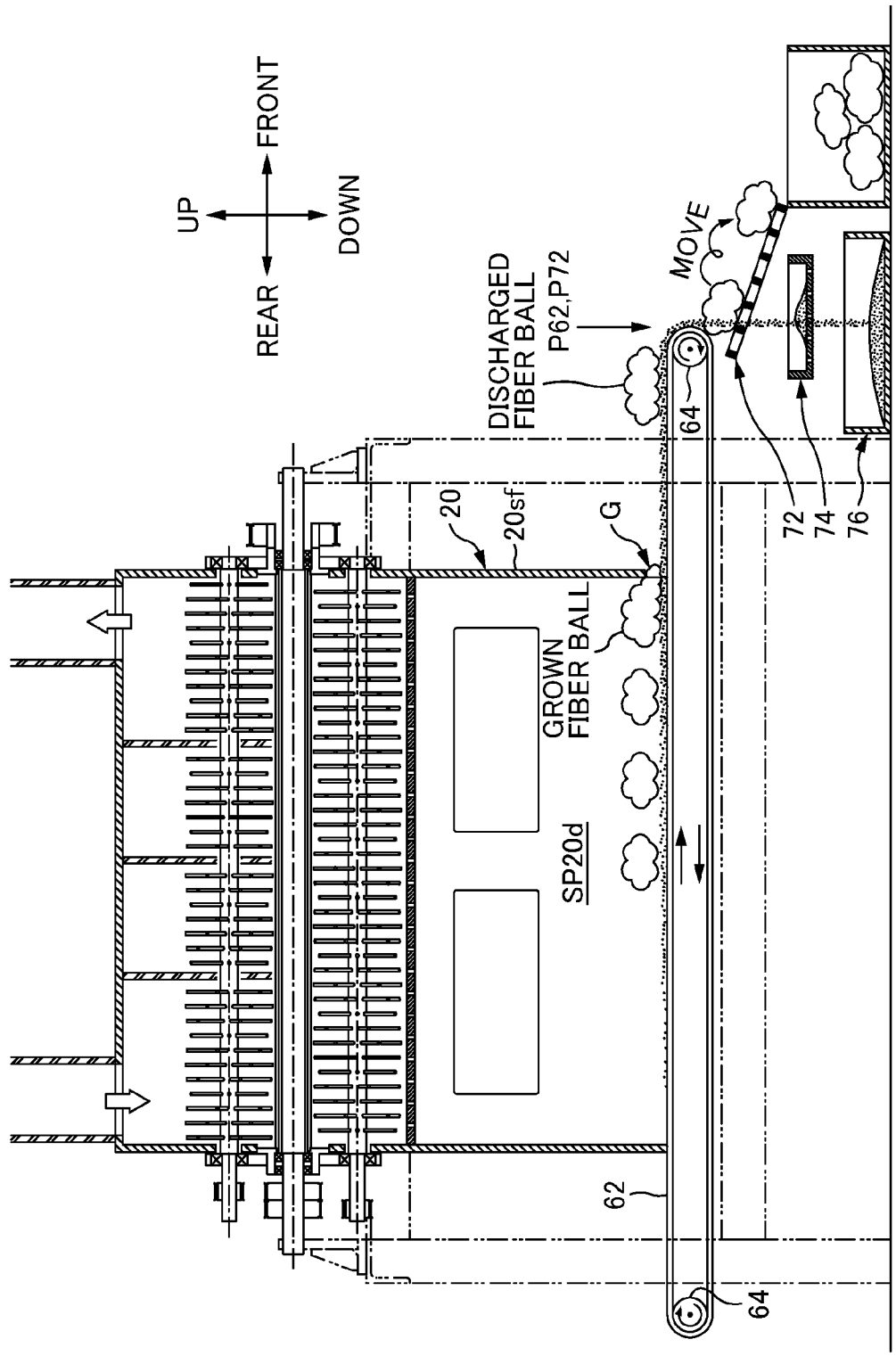
FIG. 7B is a schematic vertical sectional view showing a manner in which fiber balls formed inside the case 20 with incoming outside air is discharged to outside the case 20, and is caught in a first sieve member 72 of a separating member 70.

FIG. 7A and FIG. 7B are explanatory views showing the manner of the separation, and both figures are shown in a schematic vertical cross sectional view. As shown in FIG. 7A, first with the movement of the endless belt 62 the SAPs and the foreign matter are sent to the front to a downstream side of the movement direction, and at this time, the pulp fibers that are smaller in specific gravity than the SAPs and the foreign matter are regulated from moving to the front with the incoming outside air that flows to the rear, and thus the pulp fibers are generally rolled on the upper surface of the endless belt 62 and fiber balls are formed. Then, in this way, only the fiber balls remain inside the case 20 and only the SAPs and the foreign matter are sent to the front, and as a result the pulp fibers, the SAPs, and the foreign matter are separated.

Further, as shown in FIG. 7B, these fiber balls, during the rolling process, grow into a snowball form while entangling and intertwining the peripheral pulp fibers. Then, in the case that the fiber ball that has grown to a size corresponding to the above space G is sandwiched and jammed in the space G between both the upper surface of the endless belt 62 and the lower end edge section of the front side wall section 20sf of the case, the incoming outside air weakens, and friction between the fiber ball and the endless belt 62 increases and the like, thus the movement power to the front applied from the endless belt 62 increases relatively, and thus the fiber ball is discharged to outside the case 20 from the space G. As a result, the fiber ball in this large form is sent to the turning position P62 of the endless belt 62, and the pulp fibers which are the fiber balls are to be more certainly captured with the above described first sieve member 72.

Further, preferably, the first sieve member 72 has a transporting mechanism that transports the fiber balls that have been regulated from passing the first sieve member 72 and that have been caught to a position away from a landing position P72 from the first sieve member 72. For example, in the example in FIG. 7B, a tabular wire gauze 72 is used as the first sieve member 72, and this wire gauze 72 is arranged inclined so that its front end section on the upper surface is lower than the rear end section, thus functioning as the above described transporting mechanism. In other words, the fiber balls that have dropped on the upper surface of the wire gauze 72 which is the first sieve member 72 roll to the front due to the inclination gradient of the upper surface of the wire gauze 72, and thus the fiber balls are moved further forward than the landing position P72. Thus, the SAPs and the foreign matter that have dropped from the turning position P62 accumulating thereafter on the fiber balls have been caught with the first sieve member 72, and decreasing the sifting effect can be effectively prevented.

The transporting mechanism, however, is not limited to that described above in any way. For example, as the first sieve member 72, the endless belt (not shown) of the wire gauze form is used, and then by circulating and driving the endless belt in the wire gauze form, the fiber balls that have dropped on and that have been caught with the endless belt may be sent to the front.

By the way, preferably, as shown in FIG. 3A, regulating members 28 that regulate movement of the waste material from the insertion port 22 to the discharge port 24 may be suspended from the ceiling section 20c of the case 20, in predetermined positions in the front-rear direction in the upper space SP20u in the case 20. In the example in FIG. 3A, these regulating members 28 are arranged in three positions in the front-rear direction with intervals between them, and thus space of the upper space SP20u above the rotation member 30 is divided into four zones. In more detail, each regulating member 20 is a plate-like regulating board 28, and the thickness direction is faced in the front-rear direction, and is arranged to divide the upper space SP20u across the entire length in the left-right direction. Further, as shown in FIG. 3C, the shape of the lower end edge section of each regulating board 28 is an arc-shaped recessed shape corresponding to a rotation path Tr30 drawn by the protruding sections 33t of the shaft member 33 of the rotation member 30, and a lower end edge section 28d of the regulating board 28 is overlapped with the rotation path Tr30 of the tip end section of the protruding sections 33t in the up-down direction.

Thus, a certain extension of a holding time of the waste material in the case 20 can be achieved, and a long holding time can be secured. Then, in this way, opening of the waste material can be progressed to a sufficient level, and as a result, separation performance of the pulp fibers from the waste material can be improved, and the pulp fibers can be collected with high purity.

By the way, as already described in FIG. 3A, in this example, of the four shaft members 33, 33 . . . of the rotation member 30, in regards to the shaft members 33, 33 adjacent to each other in the revolving direction, the arrangement positions of the protruding section groups to each other are shifted in the axial direction. Thus, in this example, in respect to two shaft members 33, 33 of these four shaft members 33, 33 . . . , specific protruding section groups G33t are in positional relationships that interfere with the regulating boards 28. For example, in FIG. 3A, there was a possibility of a predetermined protruding section group G33t of the shaft member 33 shown to the upper side interfering with the regulating boards 28. Then, in this example, the protruding section groups G33t that interfere with the regulating boards 28 were taken off from the shaft members 33. This interference prevention idea is not limited to the above in any way, and for example, with increase in arrangement pitch in the axial direction of the protruding section groups G33t and by devising a method to make the thickness of the regulating boards 28 thinner and the like, the regulating boards 28 can be appropriately placed in a space between the protruding section groups G33t, G33t adjacent to each other in the front-rear direction, then the protruding section groups G33t do not have to be taken off.

Further, as described above, the number of setting the regulating boards 28 was three, but it not limited to three as described above in any way, and may be one or two, or equal to or more than four.

Further, as described above, the regulating board 28 which is made of one board is exemplified as each regulating member 28, but it is not limited to this in any way. In other words, each regulating member 28 may be configured from a plurality of members. For example, as the regulating member 28, a regulating member 28 having a plurality of sticklike members (not shown) suspended from the ceiling section 20c along the longitudinal direction downwards, and with each sticklike member configured arranged comb-like with an interval between the sticklike members adjacent in the left-right direction may be used.

Further, preferably, as shown in FIG. 2A and FIG. 2B, a suction port 29 that suctions air in the lower space SP20d may be provided. Then, in this way, the pulp fibers that have passed through the through holes h26, h26 . . . of the partition board 26 and that are floating in the lower space SP20d can be suctioned in together with air with the suction port 29, and as a result a collection rate of the pulp fiber can be increased.

In the example in FIG. 2A and FIG. 2B, the suction ports 29, 29 . . . are formed in opposing parts from the sides of the lower space SP20d of the left side wall section 20sl and the right side wall section 20sr of the case 20. Further, the suction ports 29 are formed arranged in the front-rear direction in twos as one of a plurality of examples, in respect to each of the left side wall section 20sl and the right side wall section 20sr.

Then, by providing two suction ports 29, 29 arranged in the front-rear direction in this way, a suction force distribution in the front-rear direction can be made uniform, and such as generation of a stagnation point in the lower space SP20d can be prevented, and as a result a malfunction such as the pulp fiber accumulating in a specific position in the lower space SP20d can be effectively prevented.

Further, the suction ports 29 are provided in the side wall portions 20sl, 20sr, and so the suction ports 29 suck in the air in the lower space SP20d from substantially the sides. Thus, the SAPs and the foreign matter that have dropped downwards in the lower space SP20d and that have accumulated on the endless belt 62 of the dropped object discharge mechanism 60 are generally not sucked in with the suction ports 29, and the pulp fibers floating in the air of the lower space SP20d can simply be sucked in. Then, in this way, the pulp fibers can be collected with high purity from within the lower space SP20d.

These suction ports 29 attached to these side wall sections 20sl, 20sr can be realized by connecting tip sections 29de of the suction ducts 29d provided outward of the case 20 as shown in FIG. 2B to each of the rectangular opening sections 29e formed through each of the side wall sections 20sl, 20sr. It should be noted that, each suction duct 29d is connected with a blower (not shown) via an appropriate intermediate pipe member 29m such as a hose, and in this way, the air can be sucked in from the above pipe end section.

Further, with suction of the air from the suction ports 29, the negative pressure level in the case 20 is increased, and the suction amount of air with the suction ports 29 effects the flow amount of the incoming outside air into the case 20 as described above. Thus, in view of the forming situation of the above described fiber balls, the suction amount (m$^3$/min) per unit time with the suction ports 29 is decided.

Here preferably, as shown in FIG. 2B, a pipe axis direction C29d of the suction ducts 29d faces diagonally upward in an inclined gradient that increases the further away from the case 20. Then, in this case, since the suction direction with the tip section 29de of the suction duct 29d faces diagonally upwards, with the suction force having the upward direction component, the pulp fibers in the case 20 can be sucked up. Then, in this way, the pulp fibers that have dropped onto and accumulated on the upper surface of the endless belt 62 of the dropped object discharge mechanism 60 positioned below the case 20 can also be sucked up, and this also contributes to improving the collection rate of the pulp fibers. The inclination degree θc29d from a horizontal direction from the pipe axis direction C29d is selected from a range greater than 0° and smaller than 90°, and is preferably selected from a range of 45° to 60°. By the way, when this angle is set to smaller than 45°, the SAPs and the like easily fall in the suction duct 29d and easily accumulates, and on the other hand, in the case that this angle is set to greater than 60°, attaching of the suction duct 20d becomes difficult.

It should be noted that, in the case that the pipe axis direction C29d is facing diagonally upward as above, basically, a bottom surface 29db of the suction duct 29d is formed as an inclined surface that lowers as it nears the case 20, as shown in FIG. 2B. Thus, even in the event that the SAPs and the foreign matter are sucked into the suction port 29, as long as the SAPs and the foreign matter drop on the bottom surface 29db of the suction duct 29d with its own weight, with inclination from a horizontal direction of the bottom surface 29db, the SAPs and the foreign matter slip down and are guided to return into the case 20. Then, in this way, a state in which the suction ports 29, that are to selectively suck in the pulp fibers, collecting the wrongfully sucked in SAPs and foreign matter together with the pulp fiber in the end can be effectively prevented. The inclination degree θ29db from the horizontal direction of the bottom surface 29db is selected from a range greater than 0° and smaller than 90°, and preferably is selected from a range of 45° to 60°. By the way, in the case that the angle is set smaller than 45°, it becomes difficult for the SAPs and the like to slide on the bottom surface 29db of the suction duct 29d, and easily accumulate on the bottom surface 29db, and on the other hand in the case that the angle is set greater than 60°, attachment of the suction duct 29d becomes difficult.

Further, more preferably, as shown in FIG. 2B, a suction direction in a connecting position between the suction duct 20d and the intermediate pipe member 29 is set diagonally downwards. Then, in this way, a state in which the pulp fibers that have been sucked in and collected return again into the case 20 can be certainly prevented.

It should be noted that, the opening shape of the suction port 29 is not limited to the above described rectangle in any way, and may be a circle, or a polygon other than a rectangle.

Further, in the above described example, the above suction port 29 is provided to only the left side wall section 20sl and the right side wall section 20sr, but it is not limited to this in any way. For example, the suction port 29 may be provided further to the front side wall section 20sf and the rear side wall section 20sb in addition to the left side wall section 20sl and the right side wall section 20sr, or in some cases, instead of the left side wall section 20sl and the right side wall section 20sr, the suction port 29 may be provided to both or only one of the front side wall section 20sf and the rear side wall section 20sb.

Furthermore, the part to provide the suction port 29 is not limited to each of the side wall sections 20sl, 20sr, 20sf, 20sb of the case 20 in any way. For example, it may be as shown in the modified example shown in FIG. 8A and FIG. 8B. It should be noted that, FIG. 8A is a schematic vertical section view, and FIG. 8B is a B-B arrow view in FIG. 8A.

In this modified example, a round pipe 29p as a pipe member having a suction port 29 is arranged inserted into a lower space SP20d from its front to its rear with the pipe axis direction in a position in parallel along the front-rear direction. Then, the lower surface of the round pipe 29p is formed with 12 suction ports 29, 29 . . . that pass through as one example of a plurality of ports. In more detail, this lower surface has a suction port row G29 formed with six suction ports 29, 29 . . . arranged in a row in the front-rear direction as one example of a plurality of suction ports, and this suction port row G29 is provided with only two rows as one example of a plurality of rows in the left-right direction.

Further, a pipe end section to the rear side which is the front end side of the insertion direction of the round pipe 29d is sealed airtight, but the pipe end section to the front side which is the opposite side protrudes to outside of the case 20, and this pipe end section is connected to a blower (not shown) via an appropriate intermediate pipe member 29m such as a hose.

Thus, with the operation of this blower, from each of the suction ports 29 of the round pipe 29p, the air inside the lower space SP20d is sucked in, and in this way the pulp fibers that are floating in the lower space SP20d can be collected.

It should be noted that, in this example, this round pipe 29p is arranged in a plurality of numbers (two in FIG. 8B) aligned in the left-right direction in the lower space SP20d, as shown in FIG. 8B, and in this way, a suction force distribution in the left-right direction is made uniform, but the number of the pipe is not limited to this in any way, and for example, one, or equal to or greater than three may be provided.

Further, in this example, the shape of the suction port 29 is made as a slit form having a length of 150 mm±50 mm×a width 8 to 20 mm along the longitudinal direction in the tube axis direction of the round pipe 29p, but this shape is not limited to the slit form in any way. It should be noted that, the upper limit value of the length is decided based on an anti-deformability of the round pipe 29, and the lower limit value of the width is decided from the viewpoint of prevention of clogging.

Further, in the above description, the round pipe 29p with a section shape of a circular shape as the round pipe 29p is exemplified, but it is not limited to this in any way, and for example, a square pipe with a rectangular shape in cross section may be used.

Further, in the example in FIG. 8A and FIG. 8B, the pipe end section to the rear side of the round pipe 29p is protruded to the outside of the case 20 and sealed in an airtight manner, but in some cases, the pipe end section to the rear side may be connected with an appropriate intermediate pipe member (not shown) such as a hose, and via the intermediate pipe member, may be connected to the blower connected with the above described pipe end section to the front side. In this way, the suction force becoming nonuniform, such as the suction force of the suction port 29 positioned to the rear side of the round pipe 29p becoming weaker compared to the front side, can be effectively suppressed, and in this way, over the front-rear direction of the lower space SP20d, the pulp fibers can be sucked in substantially a uniform manner.

By the way, there is a possibility that on the upper surface of this round pipe 29p, the pulp fibers, the SAP, and the foreign matter that pass through the through holes h26, h26 . . . (not shown in FIG. 8A and FIG. 8B) of the partition board 26 and drop from the upper space SP20u to the lower space SP20d will accumulate. Then, in order to avoid this accumulation, the upper section of the round pipe 29p is covered with an inclined member 29r having upper surfaces inclined with a predetermined inclination gradient from the horizontal direction. In the example in FIG. 8A and FIG. 8B, the inclined member 29r is a sectional inverted V-shaped member 29r which is a pair of flat plates connected in an inverted V-shape, for example. Then, a pointed section 29r1 of the sectional inverted V-shaped member 29r is arranged to be positioned in a central position in the left-right direction. Thus, the upper surfaces of the sectional inverted V-shaped member 29r have inclined gradients with the position of the ends lower than the central position in the left-right direction. In this way, the pulp fibers, the SAP, and the foreign matter that have dropped onto the upper surfaces, quickly slide down these upper surfaces and the above accumulation is prevented.

It should be noted that, preferably each of the end edges 29re, 29re of the sectional inverted V-shaped member 29r in the left-right direction as shown in FIG. 8B may be in a canopy form extending out to the side than the round pipe 29p. Then, in this way, this canopy form part becomes an obstacle when sucking in the dropping SAP and the foreign matter with the suction port 29, and the erroneous sucking in of the SAP and the foreign matter with the suction port 29 can be effectively prevented.

By the way, from the viewpoint of collection of the pulp fibers in the lower space SP20d with the suction port 29, preferably, as shown in FIG. 2B, the position of the upper surface of the endless belt 62 of the dropped object discharge mechanism 60 may be separated from a lowermost position P26 of the partition board 26 in regards to the up-down direction in a range of 400 to 500 mm. The reason is as follows. In other words, it is difficult to make the pulp fibers that have once landed on the endless belt 62 to again float and float in the air, and it is preferable to suck in the pulp fibers during dropping with the suction port 29 as much as possible. Thus, when separated as described above, the amount of the pulp fibers that can accumulate on the upper surface of the endless belt 62 may be significantly decreased. In this first embodiment, however, as described above, the pulp fibers that have been dropped on the endless belt 62 can be collected as fiber balls, thus by collecting as the fiber balls, the decrease of the collection rate of the pulp fibers can be prevented. By the way, the upper limit value of 500 mm is decided from the viewpoint of suppressing the separating device 10 from becoming a large size.

Second Embodiment Mode

Figure 9:
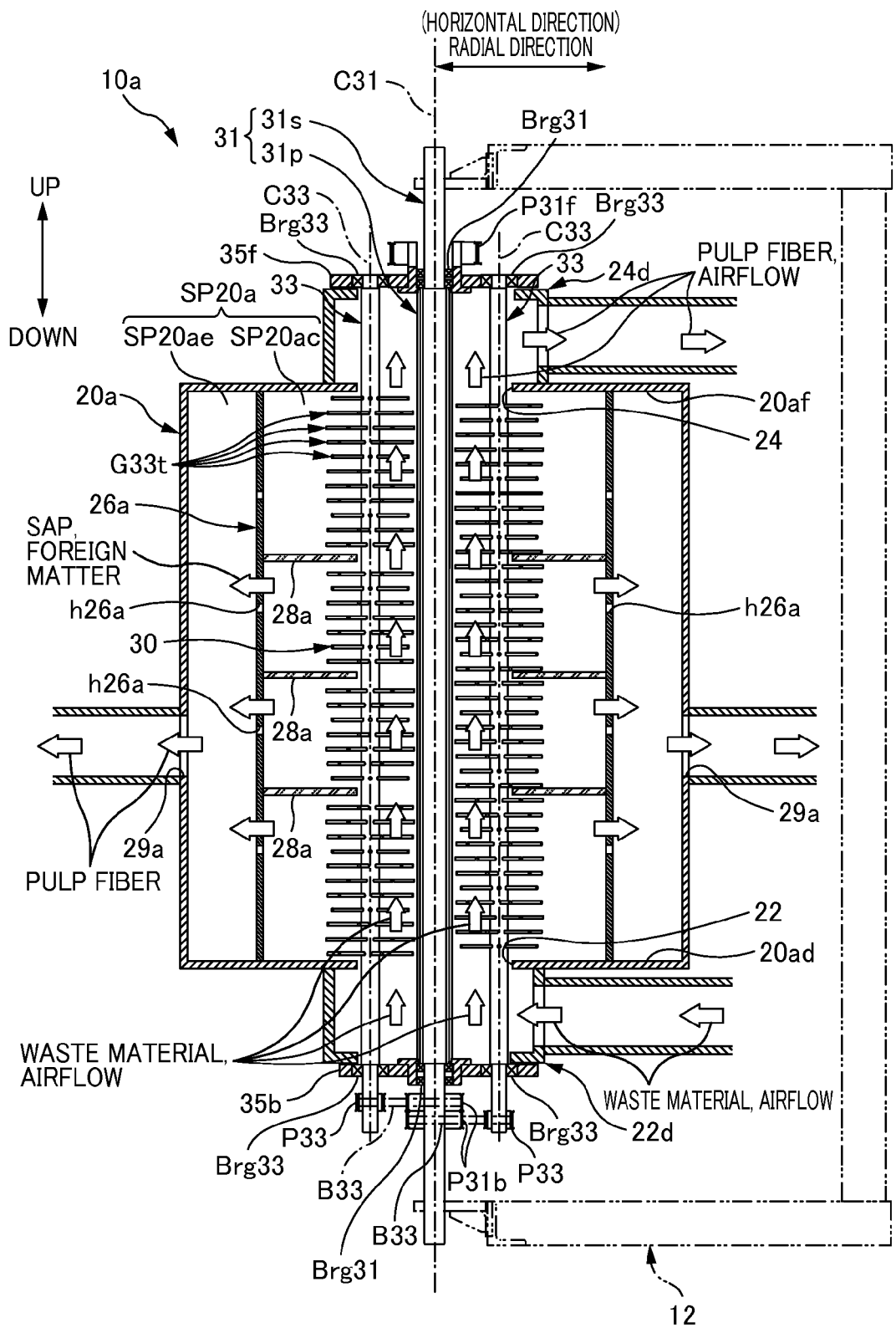
FIG. 9 is a schematic vertical sectional view of a separating device 10a in a second embodiment mode.

FIG. 9 is a schematic explanatory view of a separating device 10a of a second embodiment mode, and shows a vertical sectional view. In the first embodiment mode described above, the separating device 10 of a so-called horizontal type is exemplified. In other words, each axis direction of the revolving axis C31 and the rotating axis C33 of the shaft member 33 of the rotation member 30 are along the front to rear in the horizontal direction, but in this second embodiment mode, the separating device 10a is a vertical type, and mainly differs from the first embodiment in that, in other words the axial direction of shaft members 33 of a rotation member 30 is along the up-down direction that is a vertical direction, and also each axial direction of a revolving axis C31 and a rotating axis C33 of the shaft members 33 is along the up-down direction. It should be noted that, points other than the above, are mostly the same or similar to the first embodiment mode, and the same or similar configurations have the same reference signs attached, and description thereof will be omitted.

A case 20a is, for example, a bottomed lidded cylindrical body with the tube axis set along in parallel with the up-down direction. Then, in the inner side thereof is contained a cylindrical shaped partition member 26a, with a space in respect to an inner peripheral surface of the case 20a and substantially concentric with the case 20a, and with the partition member 26a, a space SP20a in the case 20a is divided into two of a substantially cylindrical center side space SP20ac positioned to the center side of the case 20a (corresponds to a first space), and a substantially doughnut shaped peripheral side space SP20ae (corresponds to a second space) formed by surrounding the center side space SP20ac from the peripheral side. Then, in the center side space SP20ac is housed the rotation member 30.

Here, this rotation member 30 also has four shaft members 33, 33 . . . , similar to the case of the first embodiment mode, and further, each of the shaft members 33 rotates around the rotating axis C33, and revolves around the revolving axis C31 common to each of the shaft members 33. In other words, this separating device 10a also has a mechanism to rotate and revolve each of these four shaft members 33. Specifically, this device has an outer pipe 31p and an inner shaft 31s as a revolving axis forming shaft member 31, and a pair of flange boards 35f, 35b, bearings Brg31, Brg33, pulleys P33, P31b, P31f, and endless belts B33, B31, and the like, and further, not shown in FIG. 9, also has the electric motor 37 in FIG. 2C to be drive source, a pulley P37, and an endless belt B31. Then, furthermore, each of the shaft members 33 has protruding section groups G33t, G33t in a plurality of positions in the axial direction.

In this second embodiment mode, however, as described above, the axial direction of each of the shaft members 33 is facing the up-down direction, and the revolving axis C31 of each of the shaft members 33 is also set with its axial direction in parallel with and along the up-down direction, and further the axial direction of the rotating axis C33 of each of the shaft members 33 is set in parallel with and along the up-down direction.

Further, a substantially circular bottom section 20ab of the case 20a is formed through with an insertion port 22 to communicate with the center side space SP20ac, and a substantially circular lid section 20af of the case 20a is similarly formed through with a discharge port 24 to communicate with the center side space SP20ac. Then, the insertion port 22 is connected with an insertion duct 22d with a blower, and on the other hand the discharge port 24 is also connected with a discharge duct 24d with a blower, and in this way, an airflow from the insertion port 22 to the discharge port 24 from below to above in the case 20a is formed.

Thus, in the case that the waste material is inserted from the pipe end section that is not shown of the insertion duct 22d, the waste material passes through the center side space SP20ac in the case 20a, and while passing through the waste material is agitated and opened with the rotation member 30. Then, of the waste material the pulp fibers with a small specific gravity simply rides on the airflow and is discharged from the upper discharge port 24, and on the other hand the SAP and the foreign matter with a large specific gravity is blown to the cylindrical partition member 26a to the side to the outer in the radial direction of the rotation member 30, mainly with the effect of centrifugal force applied from the rotation member 30. Here, this partition member 26a is also formed with a plurality of through holes h26a, h26a . . . similar to the case in the first embodiment mode, and the SAP and the foreign matter pass through the through holes h26a and are sent to the peripheral side space SP20ae. Then, the SAP and the foreign matter drop down this peripheral side space SP20ae with its own weight, and accumulate on the substantially doughnut-shaped bottom section 20ab of the case 20a. It should be noted that, in this example, an operator will regularly collect the accumulated SAP and the foreign matter from the bottom section 20ab of the case 20a, but in some cases, as the bottom section 20ab of the case 20a or as one part of the bottom section 20ab, an endless belt (not shown) which is a conveyor belt may be arranged, and in this way the SAP and the foreign matter may be received on the upper surface of the endless belt, and also with the circulating movement of the endless belt these SAP and foreign matter may be discharged automatically to outside the case 20a.

By the way, preferably, in respect to the separating device 10a of this second embodiment mode, in predetermined positions in the up-down direction in the center side space SP20ac, regulating members 28a that regulate movement of the waste material from the insertion port 22 to the discharge port 24 may be provided. In this example, the cylindrical partition member 26a and the rotation member 30 are arranged with an interval between each other, and the inner peripheral surface of the partition member 26a is provided with, as the regulating members 28a, substantially doughnut-shaped regulating plates 28a that protrude inward in the radial direction. Then, with the regulating plates 28a, the space between the partition member 26a and the rotation member 30 is divided into a plurality of zones in the up-down direction. Thus, the holding time of the waste material can be extended, and the waste material can be opened to a sufficient level.

Further, also in this second embodiment, there is a danger that the pulp fibers may pass through the through holes h26a, h26a . . . of the partition member 26a and enter the peripheral side space SP20ae. Thus, for the purpose of collecting the pulp fibers, preferably, in predetermined positions opposing the peripheral side space SP20ae, suction ports 29a that suck in the air of the space SP20ae are provided. In this example of FIG. 9, the plurality of the suction ports 29a, 29a . . . are positioned arranged in a substantially predetermined pitch along the peripheral direction of the case 20a. Thus, the pulp fibers can be sucked in with almost no imbalance aver the entire periphery of the peripheral side space SP20ae.

By the way, as shown in FIG. 9, in the case that the suction ports 29a are provided in positions apart from the bottom section 20ab of the case 20a by a predetermined height, then the SAP and the foreign matter accumulated on the bottom section 20ab are mostly not sucked in, and only the pulp fibers floating in the peripheral side space SP20ae can be simply selectively sucked in with the suction ports 29a. Then, in this way, the pulp fibers can be collected with a high purity.

Other Embodiment Modes

The embodiment modes of this invention have been described above, and the above embodiment modes are to facilitate understanding of this invention, and are not for limiting understanding of this invention. Further, it is needless to say that this invention may be changed and modified, without departing from the gist thereof, and this invention includes its equivalents. For example, modifications as indicated below are possible.

In the above described embodiment modes, the disposable diapers are exemplified as an example of the absorbent articles, but it is not limited to this in any way, as long as they are articles that absorb liquid such as bodily fluids, and for example the absorbent articles may be sanitary napkins, or may be pet sheets used as a place for excretion of pets.

In the above described embodiment modes, the pulp fibers are exemplified as the liquid absorbent fibers, but it is not limited thereto. In other words, as long as it is a material having a fibrous liquid absorbent ability, it may be included in the concept of the above liquid absorbent fibers.

In the above described first embodiment mode, the axial direction of the revolving axis C31 and the rotating axis C33 of the shaft members 33 of the rotation member 30 is in parallel with the front-rear direction which is a predetermined direction from the insertion port 22 to the discharge port 24, but it is not limited thereto, and may be inclined by a slight inclination angle. In other words, the axial direction may be inclined from the front-rear direction which is the predetermined direction in an inclination angle range of 0° or greater to 10° or less, or may be inclined from the front-rear direction which is the predetermined direction in an inclination angle range of 0° or greater to 5° or less, or may be inclined from the front-rear direction which is the predetermined direction in an inclination angle range of 0° or greater to 2° or less. Thus, the meaning of the wording "along" in "a revolving axis being set with an axial direction along a predetermined direction from the insertion port to the discharge port" and "a rotating axis that has been set with an axial direction along the predetermined direction" described in the claims includes not only the case in which they are parallel with each other, but also the mode in which the axes are inclined in the above described inclination angle.

In the above described embodiment modes, the rotation member 30 has four shaft members 33, 33 . . . as an example of a plurality of shaft members, but it is not limited thereto in any way. For example, the rotation member 30 may have one to three shaft members 33, or may have equal to or more than five shaft members 33, 33 . . . .

In the above described embodiment modes, the shaft member 33 has the protruding section group G33t, and the protruding section group G33t has six protruding sections 33t as one example a plurality of protruding sections, but it is not limited to this in any way. For example, the protruding section group G33t may have one to five protruding sections 33t, or may have equal to or greater than seven protruding sections 33t, 33t . . . .

In the above described embodiment modes, all four shaft members 33, 33 . . . are revolved and rotated with one electric motor 37 as the drive source, but it is not limited to this in any way. For example, the electric motor to revolve the shaft members 33 and the electric motor to rotate them may be provided separately, and further each of the shaft members 33 may have an electric motor for rotating.

In the above described embodiment modes, the material of the case 20, 20a is not mentioned, but the case 20, 20a may preferably be formed with a resin board or a glass board that is colorless and transparent, colored and transparent, colorless and translucent, or colored and translucent. In that case, the opening state in the cases 20, 20a can be made visible from the outside through the case 20, 20a. Then, in this way, an abnormality such as clogging of the waste material can be detected in an early stage, and can be handled before becoming a major problem.

REFERENCE SIGNS LIST 10 separating device
10a separating device
12 frame-like supporting member
20 case
20a case
20ab bottom section
20af lid section
20c ceiling section
20sb rear side wall section
20sf front side wall section
20sl left side wall section
20sr right side wall section
22 insertion port
22d insertion duct
24 discharge port
24d discharge duct
26 partition board (partition member)
26a partition member
28 regulating board (regulating member)
28a regulating board (regulating member)
28d lower side edge section
29 suction port
29a suction port
29d duct
29db bottom surface
29de tip section
29e opening section
29m intermediate pipe member
29p round pipe (pipe member)
29r inclined member 29*rl* pointed section
29*re* end edge
30 rotation member
31 revolving axis forming shaft member
31*p* outer pipe
31*s* inner shaft
33 shaft member
33*t* sticklike member (protruding section)
35*b* flange board
35*f* flange board
37 electric motor
60 dropped object discharge mechanism
62 endless belt
64 roller
70 separating member
72 first sieve member
74 second sieve member
76 lidless container
130 rotation member
133 rectangular plate (protruding section)
B31 endless belt
B33 endless belt
G29 suction port row
G33*t* protruding section group
Brg31 bearing
Brg33 bearing
h26 through hole
h26*a* through hole
h72 through hole
h74 through hole
GND ground section
G gap
C31 revolving axis
C33 rotating axis
C130 rotation axis
SP20 space
SP20*u* upper space (first space)
SP20*d* lower space (second space)
SP20*a* space
SP20*ac* center side space (first space)
SP20*ae* peripheral side space (second space)
P31*b* pulley
P31*f* pulley
P33 pulley
P37 pulley
P62 turning position
P72 landing position
P26 lowermost position
G gap

The invention claimed is:
1. A separating device configured to separate liquid absorbent fibers for an absorbent article from a material including the liquid absorbent fibers and impurities, the separating device comprising:
  a case;
  an insertion port configured to insert the material into the case on an insert airflow;
  a rotation member housed in the case and configured to agitate and open the material; and
  a discharge port configured to discharge, the liquid absorbent fibers of the material that has been opened with the rotation member, from inside the case, on a discharge airflow,
wherein
  the rotation member is configured to revolve, in a revolving direction, around a revolving axis extending along a predetermined direction from the insertion port to the discharge port,
  the rotation member has a plurality of shaft members arranged in the revolving direction of the rotation member,
  each of the plurality of shaft members is configured to rotate, in a rotating direction, around a rotating axis extending along the predetermined direction and to rotate along a circular path centered at the revolving axis, while the rotation member is revolving around the revolving axis in the revolving direction, and
  each of the plurality of shaft members has a protruding section group including a plurality of protruding sections arranged in the rotating direction and protruding outward in a direction that intersects with the rotating axis of the shaft member.

2. The separating device according to claim 1, wherein
in respect to the protruding section groups adjacent to each other along the rotating axis of each of the plurality of shaft members, arrangement positions of the protruding sections with respect to each other are shifted in the rotating direction.

3. The separating device according to claim 1, wherein
in respect to the shaft members adjacent to each other in the revolving direction of the rotation member, arrangement positions of the protruding section groups with respect to each other are shifted along the rotating axis of each of the adjacent shaft members.

4. The separating device according to claim 1, wherein
the revolving direction of the rotation member and the rotating direction of the plurality of shaft members are the same.

5. The separating device according to claim 1, wherein
the protruding sections are stick-shaped members,
each of the stick-shaped members is elongated in the direction that intersects with the rotating axis of the corresponding shaft member, and
each of the stick-shaped members is arranged on a peripheral surface of the corresponding shaft member.

6. The separating device according to claim 1, wherein
the case has
  a partition member having a plurality of through holes, and
  a first space and a second space separated from the first space by the partition member,
the insertion port and the discharge port are in communication with the first space,
the rotation member is housed inside the first space,
the through holes of the partition member are configured to restrict the liquid absorbent fibers from passing through and allow granular superabsorbent polymers of the material to pass through, and
the case includes a further discharge port in the second space, said further discharge port is configured to allow the superabsorbent polymers that have passed through the through holes and that have entered into the second space to be discharged to outside of the case.

7. The separating device according to claim 6, wherein
the second space is adjacent to and below the first space,
the insertion port and the discharge port are provided in a ceiling section of the case,
the separating device further comprises a regulating member suspended from the ceiling section of the case, and in a predetermined position between the insertion port and the discharge port in the first space, the regulating member is configured to regulate movement of the material from the insertion port to the discharge port.

8. The separating device according to claim 6, further comprising a suction port in the second space, wherein
said suction port is configured to suction air from inside the second space, and
the liquid absorbent fibers that have passed the through holes of the partition member and float inside the second space are sucked by the suction port.

9. The separating device according to claim 6, wherein the through holes of the partition member include
first through holes opposing the insertion port and being circular holes,
second through holes opposing the discharge port and having a larger opening area than the circular holes, and said second through holes having a longitudinal direction and a transverse direction, and
the longitudinal direction of the second through holes intersects the revolving direction of the rotation member.

10. A method of separating liquid absorbent fibers for an absorbent article from a material having the liquid absorbent fibers and impurities, the method comprising:
inserting the material into a case from an insertion port on an insert airflow;
agitating and opening the material with a rotation member housed inside the case; and
discharging the liquid absorbent fibers of the material that has been opened with the rotation member, from inside the case via a discharge port on a discharge airflow,
wherein
the rotation member revolves, in a revolving direction, around a revolving axis extending along a predetermined direction from the insertion port to the discharge port,
the rotation member has a plurality of shaft members arranged in the revolving direction of the rotation member,
each of the plurality of shaft members rotates, in a rotating direction, around a rotating axis extending the predetermined direction and rotates along a circular path centered at the revolving axis, while the rotation member is revolving around the revolving axis in the revolving direction,
each of the plurality of shaft members has a protruding section group including a plurality of protruding sections arranged in the rotating direction and protruding outward in a direction that intersects with the rotating axis of the shaft member.

\* \* \* \* \*